US007915420B2

(12) United States Patent
Huang et al.

(10) Patent No.: US 7,915,420 B2
(45) Date of Patent: Mar. 29, 2011

(54) ARYL PIPERIDINE AMIDES

(75) Inventors: Charles Q. Huang, San Diego, CA (US); Timothy W. Lovenberg, San Diego, CA (US); Alejandro Santillán, Jr., San Diego, CA (US); Liu Y. Tang, San Diego, CA (US); Ronald L. Wolin, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 921 days.

(21) Appl. No.: 11/780,133

(22) Filed: Jul. 19, 2007

(65) Prior Publication Data

US 2008/0009521 A1     Jan. 10, 2008

Related U.S. Application Data

(62) Division of application No. 10/919,734, filed on Aug. 17, 2004, now Pat. No. 7,276,610.

(60) Provisional application No. 60/498,477, filed on Aug. 27, 2003.

(51) Int. Cl.
*A61K 31/4535* (2006.01)
*C07D 211/04* (2006.01)
*C07D 409/02* (2006.01)

(52) U.S. Cl. ........ 546/206; 548/517; 544/144; 544/146; 544/224; 514/326; 514/218; 514/231.5

(58) Field of Classification Search .................. 546/206; 548/517; 544/145, 146, 224; 514/326, 218, 514/231.5
See application file for complete search history.

(56) References Cited

FOREIGN PATENT DOCUMENTS

EP      1069113       1/2001
WO    WO 01/85694    11/2001

OTHER PUBLICATIONS

Caulfield, W.L. et al., "The first potent and selective inhibitors of the glycine transporter type 2", Journal of Medicinal Chemistry, American Chemical Society, Washington, US, vol. 44, No. 17, Aug. 2001, pp. 2679-2683.
Combs, A.P. et al., "Protein Structure-Based Combinatorial Chemistry: Discovery of Non-Peptide Binding Elements to SRC SH3 Domain", Journal of the American Chemical Society, American Chemical Society, Washington DC, US, vol. 118, 1996, pp. 287-288.
Evans, J. et al. Cloning, Functional Characterization and Population Analysis of a Variant Form of the Human Glycine Type 2 Transporter. FEBS Lett. 1999, 463(3):301-306.
Friauf, E. et al. Developmental Expression of the Glycine Transporter GLYT2 in the Auditory System of Rats Suggests Involvement in Synapse Maturation. J. Comp. Neurol. 1999, 412(1):17-37.
Gallagher, M.J. et al. Characterization of Multiple Forms of the Human Glycine Transporter Type-2. Mol. Brain Res. 1999, 70(1):101-115.
Geerlings, A. et al. Characterization of the Interactions Between the Glycine Transporters GLYT1 and GLYT2 and the SNARE protein syntaxin 1A. FEBS Letters 2000, 470:51-54.
Grenningloh, G. et al. The Strychnine-binding Subunit of the Glycine Receptor Shows Homology with Nicotinic Acetylcholine Receptors. Nature (London) 1987, 328(16):215-220.
Guastella, J. et al. Cloning, Expression, and Localization of a Rat Brain High-Affinity Glycine Transporter. Proc. Natl. Acad. Sci. U.S.A. 1992, 89(15):7189-7193.
Huang, W. and R.K. Simpson. Long-term Intrathecal Administration of Glycine Prevents Mechanical Hyperalgesia in a Rat Model of Neuropathic Pain. Neurol. Res. 2000, 22:160-164.
Isaac et al., "5, 5-Diaryl-2-amino-4-pentenoates as novel, potent, and selective glycine transporter type-2 reuptake inhibitors", Bioorganic & Medicinal Chemistry Letters, Oxford, GB, vol. 11, 2001, pp. 1371-1373.
Isaac, M. Synthesis and Structure Activity Relationship of Novel Chiral Ligans for the Glycine-Reuptake Transporter Type-2 (GlyT-2). Abstracts of Papers, 228th ACS National Meeting, Philadelphia, PA, U.S., Aug. 22-26, 2004.
Iversen, L.L. Role of Transmitter Uptake Mechanism in Synaptic Neurotransmission. Br. J. Pharmacol. 1971, 41(4):571-591.
Krnjevic, K. Chemical Nature of Synaptic Transmission in Vertebrates. Physiol. Rev. 1974, 54(2):418-540.
Liu, Q-R. et al. Cloning and Expression of a Spinal Cord- and Brian-Specific Glycine Transporter with Novel Structural Features. J. Biol. Chem. 1993, 268(30):22802-22808.
Lopez-Corcuera, B. et al. Differential Properties of Two Stably Expressed Brain-Specific Glycine Transporters. J. Neurochem. 1998, 71(5):2211-2219.
Luque, J.M. et al. Cellular Expression of Glycine Transporter 2 Messenger RNA Exclusively in Rat Hindbrain and Spinal Cord. Neuroscience 1995, 64(2):525-535.
Ponce, J. et al. Transmembrane Domaine III Plays an Important Role in Ion Binging and Permeation in the Glycine Tranporter GLYT2. J. Biol. Chem. 2000, 275(18):13856-13862.
Probst, A. et al. The Distribution of Glycine Receptors in the Human Brain. A Light Microscopic Autoradiographic Study Using [3H]Strychnine. Neuroscience 1986, 17(1):11-35.
Raiteri, L. et al. Glycine Taken Up Through GLYT1 and GLYT2 Heterotransporters into Glutamatergic Axon Terminals of Mouse Spinal Cord Elicits Release of Glutamate by Homo-Transporter Reversal and Through Anion Channels. Biochem. Pharm. 2005, 69(1):159-168.
Rajendra, S. and P.R. Schofield. Molecular Mechanisms of Inherited Startle Syndromes. Trends Neurosci. 1995, 18(2):80-82.
Simpson, R.K., Jr. et al. Reduction in the Mechanonociceptive Response by Intrathecal Administration of Glycine and Related Compounds. Neurochem. Res. 1996, 21(10):1221-1226.
Wolin, R.L. et al., "Inhibitors of the glycine transporter type-2 (GlyT-2): syntehsis and biological activity of benzoylpiperidine derivatives", Bioorganic and Medicinal Chemistry, vol. 12, 2004, pp. 4511-4532.
Wolin, R.L. Novel Glycine Transporter Type-2 Reuptake Inhibitors. Part 1: a-Amino Acid Derivatives. Bioorg. Med. Chem. 2004, 12(16):4477-4492.

(Continued)

Primary Examiner — Rita J Desai
(74) Attorney, Agent, or Firm — John Harbour

(57) ABSTRACT

The invention provides novel GlyT2 inhibiting compounds useful in modulating, treating, or preventing: anxiolytic disorders; a condition requiring treatment of injured mammalian nerve tissue; a condition amenable to treatment through administration of a neurotrophic factor; a neurological disorder; or obesity; an obesity-related disorder.

6 Claims, No Drawings

OTHER PUBLICATIONS

Young, A.B. and S.H. Snyder. Strychnine Binding Associated with Glycine Receptors of the Central Nervous System. Proc. Natl. Acad. Sci. U.S.A. 1973, 70(10):2832-2836.

Zarbin, M.A. et al. Glycine Receptor: Light Microscopic Autoradiographic Localization with [3H]Strychnine. J. Neurosci. 1981, 1(5):532-547.

ARYL PIPERIDINE AMIDES

This application is a divisional of application Ser. No. 10/919,734 filed Aug. 17, 2004 now U.S. Pat. No. 7,276,610, which in turn claims the benefit of U.S. provisional application Ser. No. 60/498,477 filed Aug. 27, 2003. The complete disclosures of the aforementioned related U.S. patent applications are hereby incorporated herein by reference for all purposes.

FIELD OF THE INVENTION

This invention relates to modulators of the type 2 glycine transporter (GlyT2). More particularly, this invention relates to certain piperidine amides useful as selective GlyT2 inhibitors for the treatment of central nervous system (CNS) conditions such as muscle spasticity, tinnitus, epilepsy and neuropathic pain.

BACKGROUND OF THE INVENTION

Glycine, along with γ-aminobutyric acid (GABA), is primarily responsible for inhibiting neurotransmission in the CNS. Additionally, glycine is an essential co-agonist at the N-methyl-D-aspartate (NMDA) receptor where it acts to attenuate the excitatory actions of glutamate (L. L. Iverson, *Br. J. Pharmacol.* 1971, 41(4):571-591).

Radio-labeled strychnine binding studies (A. B. Young and S. H. Snyder, *Proc. Natl. Acad. Sci. U.S.A.* 1973, 70(10): 2832-2836; M. A. Zarbin et al., *J. Neurosci.* 1981, 1(5):532-547; A. Probst et al., *Neuroscience* 1986, 17(1):11-35; H. Betz, *Nature* 1987, 328(16):215-220) provide strong evidence that glycie is the major inhibitory amino acid operating in the brainstem and spinal cord of vertebrates, and exerts its effects post-synaptically at the strychnine-sensitive glycinergic receptor (K. Krnjevic, *Physiol. Rev.* 1974, 54(2):418-540).

The binding of glycine to its specific receptor induces the opening of a ligand-gated chloride channel, which results in an influx of chloride ion into the post-synaptic neuron. This process causes the neuron to become hyperpolarized, and ultimately raises the threshold for neuronal signaling. The physiological effects of glycine are regulated by glycine transporters, which provide a mechanism for the re-uptake of glycine from the synaptic cleft back into the pre-synaptic neuron and surrounding glial cells.

Currently there are two known glycine transporters expressed in the CNS: GlyT1 and GlyT2 (J. Guastella et al., *Proc. Natl. Acad. Sci. USA* 1992, 89(15):7189-7193; Q.-R. Liu et al., *J. Biol. Chem.* 1993, 268(30):22802-22808; B. Lopez-Corcuera et al., *J. Neurochem.* 1998, 71(5):2211-2219). Separate genes encode each transporter, and the transporters have distinctly different pharmacologies as evidenced by their sensitivities to sarcosine (N-methylglycine) (B. López-Corcuera et al., *J. Neurochem.* 1998, 71(5):2211-2219). Both the rat and human GlyT2 transporters have been cloned and share ~93% sequence homology at the amino acid level (M. J. Gallagher et al., *Mol. Brain. Res.* 1999, 70(1): 101-115; J. Evans et al., *FEBS Lett.* 1999, 463(3):301-306). Biochemical evidence gathered thus far suggests that the GlyT2 transporter is closely associated with the strychnine-sensitive glycine receptors in the brainstem and spinal cord.

GlyT2 inhibitors should prevent glycine reuptake and accentuate the post-synaptic inhibitory activity of the glycineric receptor, and may thus be useful in the treatment of CNS conditions associated with glycinergic receptor malfunction, such as muscle spasticity, tinnitus, epilepsy and neuropathic pain (E. Friauf et al., *J. Comp. Neurol.* 1999, 412(1):17-37; R. K. Simpson et al., *Neurochem. Res.* 1996, 21(10):1221-1226; W. Huang and R. K. Simpson, *Neurological Res.* 2000, 22:160-164).

SUMMARY OF THE INVENTION

The invention provides GlyT2 inhibitors of the formula (I):

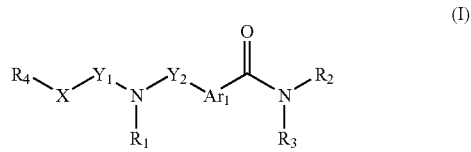

wherein
$R_1$ is H or is a substituted or unsubstituted $C_{1-5}$ alkyl, $C_{1-5}$ alkenyl, or $C_{1-5}$ alkynyl;
$R_2$ and $R_3$ are independently selected from H, $C_{1-6}$ alkyl, $C_{1-6}$ alkenyl, $C_{1-6}$ alkynyl, or, alternatively, $R_2$ and $R_3$ may be taken together with the nitrogen of attachment to form piperidinyl, pyrrolidinyl, pyrrolinyl, tetrahydropyridinyl, dihydropyridinyl, azepanyl or morpholinyl, wherein each $R_2$ and $R_3$ substituent separately or taken together, is optionally substituted with hydroxy or $C_{1-4}$alkoxy;
$R_4$ is phenyl optionally substituted at the 2 or 3 position with one or two $R^q$;
$Ar_1$ is phenylene, pyridinediyl, pyrimidinediyl, thiophenediyl or thiazolediyl, optionally substituted with $R^q$;
$Y_1$ and $Y_2$ are independently selected from a $C_{1-5}$ alkandiyl or a $C_{1-5}$ alkenediyl;
X is S, O, or is $NR_1$, or alternatively, is a covalent bond; and
$R^q$ is selected from the group consisting of —OH, —$C_{1-6}$ alkyl, —$OC_{1-6}$ alkyl, -Ph, -PhOH, -ureaPh, —OPh, benzyl, —Obenzyl, -ureabenzyl, thiophenyl, —$C_{3-6}$ cycloalkyl, —$OC_{3-6}$ cycloalkyl, —CN, —$NO_2$, —$N(R^y)R^z$ (wherein $R^y$ and $R^z$ are independently selected from the group consisting of H, $C_{1-6}$alkyl and $C_{1-6}$ alkenyl, or $R^y$ and $R^z$ may be taken together with the nitrogen of attachment to form an otherwise aliphatic hydrocarbon ring, said ring having 4 to 7 members, optionally having one carbon replaced with O, =N—, NH, or N($C_{1-4}$alkyl), optionally having one carbon substituted with —OH, and optionally having one or two unsaturated bonds in the ring), —(C=O)N($R^y$)$R^z$, —(N—$R^t$)COR$^t$, —(N—$R^t$)$SO_2C_{1-6}$alkyl (wherein $R^t$ is independently H or $C_{1-6}$alkyl or two $R^t$ in the same substituent may be taken together with the amide of attachment to form an otherwise aliphatic hydrocarbon ring, said ring having 4 to 6 members), —(C=O)$C_{1-6}$alkyl, —(S=(O)n)—$C_{1-6}$alkyl (wherein n is selected from 0, 1 or 2), —$SO_2N(R^y)R^z$, —$SCF_3$, halo, —$CF_3$, —$OCF_3$, —COOH and —$COOC_{1-6}$ alkyl;
and stereoisomers, pharmaceutically acceptable salts, solvates, and polymorphs thereof.

The invention also provides pharmaceutical compositions, methods of treatment, and syntheses relating to the novel GlyT2 inhibitors.

DETAILED DESCRIPTION OF THE INVENTION

In preferred embodiments, the invention provides compounds of formula (I) in which, independently:
$R_1$ is H; $R_2$ and $R_3$ together with the nitrogen of attachment form piperidinyl; $R_4$ is phenyl and is substituted at the 2 or 3 position with an —OC$_{1-6}$ alkyl or —N(R$^y$)R$^z$, wherein R$^y$ and R$^z$ are independently a C$_{1-6}$ alkyl; Ar$_1$ is phenylene; Y$_1$ and Y$_2$ are the same or different and are methylene or ethylene; and X is NH or O.

In a particularly preferred embodiment, the invention provides compounds of formula (I) in which, independently: R$_1$ is H; R$_2$ and R$_3$ together with the nitrogen of attachment form piperidinyl; R$_4$ is phenyl and is substituted at the 2 or 3 position with propoxy; Ar$_1$ is phenylene; Y$_1$ is ethylene and Y$_2$ is methylene; and X is NH or O.

A preferred formula (I) is given by formula (Ia):

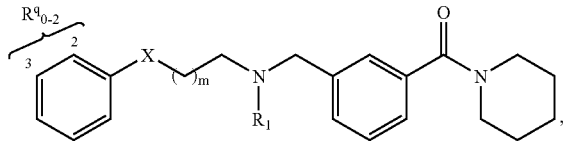

where m is 1 or 2.

Compounds of the invention include, but are not limited to, the following:

(3-{[2-(2-Isopropoxy-phenylamino)-ethylamino]-methyl}-phenyl)-piperidin-1-yl-methanone;
(3-{[3-(2-Isopropoxy-phenylamino)-propylamino]-methyl}-phenyl)-piperidin-1-yl-methanone;
{3-[(2-Phenylamino-ethylamino)-methyl]-phenyl}-piperidin-1-yl-methanone;
(3-{[2-(2-Hydroxy-phenylamino)-ethylamino]-methyl}-phenyl)-piperidin-1-yl-methanone;
(3-{[2-(2-Methoxy-phenylamino)-ethylamino]-methyl}-phenyl)-piperidin-1-yl-methanone;
[3-({2-[2-(1-Ethyl-propoxy)-phenylamino]-ethylamino}-methyl)-phenyl]-piperidin-1-yl-methanone;
(3-{[2-(2-Cyclopentyloxy-phenylamino)-ethylamino]-methyl}-phenyl)-piperidin-1-yl-methanone;
(3-{[2-(2-Phenoxy-phenylamino)-ethylamino]-methyl}-phenyl)-piperidin-1-yl-methanone;
(3-{[2-(3-Methoxy-phenylamino)-ethylamino]-methyl}-phenyl)-piperidin-1-yl-methanone;
(3-{[2-(3-Isopropoxy-phenylamino)-ethylamino]-methyl}-phenyl)-piperidin-1-yl-methanone;
(3-{[2-(2-Amino-phenylamino)-ethylamino]-methyl}-phenyl)-piperidin-1-yl-methanone;
(3-{[2-(2-Isopropylamino-phenylamino)-ethylamino]-methyl}-phenyl)-piperidin-1-yl-methanone;
N-(2-{2-[3-(Piperidine-1-carbonyl)-benzylamino]-ethylamino}-phenyl)methanesulfonamide;
1-Phenyl-3-(2-{2-[3-(piperidine-1-carbonyl)-benzylamino]-ethylamino}-phenyl)-urea;
1-Benzyl-3-(2-{2-[3-(piperidine-1-carbonyl)-benzylamino]-ethylamino}-phenyl)-urea;
(3-{[2-(2-Bromo-phenylamino)-ethylamino]-methyl}-phenyl)-piperidin-1-yl-methanone;
(3-{[2-(3-Bromo-phenylamino)-ethylamino]-methyl}-phenyl)-piperidin-1-yl-methanone;
(3-{[2-(2-Chloro-phenylamino)-ethylamino]-methyl}-phenyl)-piperidin-1-yl-methanone;
(3-{[2-(3-Chloro-phenylamino)-ethylamino]-methyl}-phenyl)-piperidin-1-yl-methanone;
(3-{[2-(2-Isopropyl-phenylamino)-ethylamino]-methyl}-phenyl)-piperidin-1-yl-methanone;
(3-{[2-(2'-Methoxy-biphenyl-2-ylamino)-ethylamino]-methyl}-phenyl)-piperidin-1-yl-methanone;
Piperidin-1-yl-(3-{[2-(2-thiophen-3-yl-phenylamino)-ethylamino]-methyl}-phenyl)-methanone;
(3-{[2-(2-Isopropoxy-phenoxy)-ethylamino]-methyl}-phenyl)-piperidin-1-yl-methanone;
(3-{[3-(2-Isopropoxy-phenoxy)-propylamino]-methyl}-phenyl)-piperidin-1-yl-methanone;
(3-{[2-(3-Isopropoxy-phenoxy)-ethylamino]-methyl}-phenyl)-piperidin-1-yl-methanone;
[3-({[2-(2-Isopropoxy-phenylamino)-ethyl]-methyl-amino}-methyl)-phenyl]-piperidin-1-yl-methanone;
[3-({2-[(2-Isopropoxy-phenyl)-methyl-amino]-ethylamino}-methyl)-phenyl]-piperidin-1-yl-methanone;
{3-[({2-[(2-Isopropoxy-phenyl)-methyl-amino]-ethyl}-methyl-amino)-methyl]-phenyl}-piperidin-1-yl-methanone
[3-({[2-(3-Isopropoxy-phenylamino)-ethyl]-methyl-amino}-methyl)-phenyl]-piperidin-1-yl-methanone;
{3-[({2-[(3-Isopropoxy-phenyl)-methyl-amino]-ethyl}-methyl-amino)-methyl]-phenyl}-piperidin-1-yl-methanone;
(3-{[2-(2-Isopropoxy-phenylsulfanyl)-ethylamino]-methyl}-phenyl)-piperidin-1-yl-methanone;
(3-{[3-(2-Isopropoxy-phenyl)-propylamino]-methyl}-phenyl)-piperidin-1-yl-methanone;
(5-{[2-(2-Isopropoxy-phenylamino)-ethylamino]-methyl}-thiophen-3-yl)-piperidin-1-yl-methanone;
(5-{[2-(2-Amino-phenylamino)-ethylamino]-methyl}-thiophen-3-yl)-piperidin-1-yl-methanone;
(5-{[2-(2-Isopropylamino-phenylamino)-ethylamino]-methyl}-thiophen-3-yl)piperidin-1-yl-methanone;
N,N-Diethyl-3-{[2-(2-isopropoxy-phenylamino)-ethylamino]-methyl}-benzamide;
(3-{[2-(2-Isopropoxy-phenylamino)-ethylamino]-methyl}-phenyl)-pyrrolidin-1-yl-methanone;
Azepan-1-yl-(3-{[2-(2-isopropoxy-phenylamino)-ethylamino]-methyl}-phenyl)methanone;
(3-{[2-(2-Isopropoxy-phenylamino)-ethylamino]-methyl}-phenyl)-morpholin-4-yl-methanone; and
(4-Hydroxy-piperidin-1-yl)-(3-{[2-(2-isopropoxy-phenylamino)-ethylamino]-methyl}-phenyl)-methanone,
and stereoisomers, optical isomers, anomers, pharmaceutically acceptable salts, solvates, and polymorphs thereof.

Compounds of the invention are effective in modulating or treating: anxiolytic disorders; a condition requiring treatment of injured mammalian nerve tissue; a condition amenable to treatment through administration of a neurotrophic factor; a neurological disorder; obesity; or an obesity-related disorder. These disorders or conditions are defined hereinafter. For example, in certain embodiments, compounds of the invention can be used as anticonvulsants, antiepileptics, neuroprotective agents, and muscle relaxants.

As used herein, the following terms have the following respective meanings. Other terms that are used to describe the present invention have the same definitions as those generally used by those skilled in the art.

Specific examples recited in any definition are not intended to be limiting in any way.

"Hydrocarbon" refers to a substituted or unsubstituted organic compound.

"Acetal" refers to a compound in which two ether oxygens are bound to the same carbon. A "ketal" is an acetal derived from a ketone.

"Acyl" means a compound of the formula RCO, where R is aliphatic (characterized by a straight chain of carbon atoms), alicyclic (a saturated hydrocarbon containing at least one ring), or aromatic.

"Acyloxy" refers to the groups alkyl-C(O)O—, substituted alkyl-C(O)O—, cycloalkyl-C(O)O—, substituted cycloalkyl-C(O)O—, aryl-C(O)O—, hetero-aryl-C(O)O—, and heterocyclic-C(O)O— wherein alkyl, substituted alkyl, cycloalkyl, substituted cycloalkyl, aryl, heteroaryl, and heterocyclic are as defined herein.

"Alkyl" refers to a fully saturated monovalent hydrocarbon radical containing carbon and hydrogen which may be a straight chain, branched, or cyclic. Examples of alkyl groups are methyl, ethyl, n-butyl, n-heptyl, isopropyl, 2-methylpropyl, cyclopropyl, cyclopropylmethyl, cyclobutyl, cyclopentyl, cyclopentylethyl and cyclohexyl. "Cycloalkyl" groups refer to cyclic alkyl groups such as cyclopropyl, cyclobutyl, cyclopentyl and cyclohexyl. $C_1$-$C_7$ alkyl groups are preferably used in the present invention.

"Substituted alkyl" refers to alkyls as just described which include one or more functional groups such an alkyl containing from 1 to 6 carbon atoms, preferably a lower alkyl containing 1-3 carbon atoms, aryl, substituted aryl, acyl, halogen (i.e., alkyl halos, e.g., $CF_3$), hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like. The term "substituted cycloalkyl" has essentially the same definition as and is subsumed under the term "substituted alkyl" for purposes of describing the present invention.

"Amine" refers to aliphatic amines, aromatic amines (e.g., aniline), saturated heterocyclic amines (e.g., piperidine), and substituted derivatives such as an alkyl morpholine. "Amine" as used herein includes nitrogen-containing aromatic heterocyclic compounds such as pyridine or purine.

"Aralkyl" refers to an alkyl group with an aryl substituent, and the term "aralkylene" refers to an alkenyl group with an aryl substituent. The term "alkaryl" refers to an aryl group that has an alkyl substituent, and the term "alkarylene" refers to an arylene group with an alkyl substituent. The term "arylene" refers to the diradical derived from aryl (including substituted aryl) as exemplified by 1,2-phenylene, 1,3-phenylene, 1,4-phenylene, 1,2-naphthylene and the like.

"Alkenyl" refers to a branched or unbranched hydrocarbon group typically although not necessarily containing 2 to about 24 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, preferably two to four carbon atoms.

"Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

"Aryl" refers to a substituted or unsubstituted monovalent aromatic radical having a single ring (e.g., phenyl) or multiple condensed rings (e.g., naphthyl). Other examples include heterocyclic aromatic ring groups having one or more nitrogen, oxygen, or sulfur atoms in the ring, such as imidazolyl, furyl, pyrrolyl, pyridyl, thienyl and indolyl, among others. Therefore, "aryl" as used herein includes "heteroaryls" having a mono- or polycyclic ring system which contains 1 to 15 carbon atoms and 1 to 4 heteroatoms, and in which at least one ring of the ring system is aromatic. Heteroatoms are sulfur, nitrogen or oxygen.

"Substituted aryl" refers to an aryl as just described that contains one or more functional groups such as lower alkyl, acyl, aryl, halogen, alkylhalos (e.g., $CF_3$), hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like.

"Alkynyl" as used herein refers to a branched or unbranched hydrocarbon group typically although not necessarily containing 2 to about 24 carbon atoms and at least one triple bond, such as ethynyl, n-propynyl, isopropynyl, n-butynyl, isobutynyl, octynyl, decynyl, and the like. Generally, although again not necessarily, alkynyl groups herein contain 2 to about 12 carbon atoms. The term "lower alkynyl" intends an alkynyl group of two to six carbon atoms, preferably three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

"Alkoxy" as used herein refers to an alkyl group bound through an ether linkage; that is, an "alkoxy" group may be represented as —O— alkyl where alkyl is as defined above. A "lower alkoxy" group intends an alkoxy group containing one to six, more preferably one to four, carbon atoms.

"Allenyl" is used herein in the conventional sense to refer to a molecular segment having the structure —CH=C=$CH_2$. An "allenyl" group may be unsubstituted or substituted with one or more non-hydrogen substituents.

"Anomer" as used herein means one of a pair of isomers of a cyclic carbohydrate resulting from creation of a new point of symmetry when a rearrangement of atoms occurs at an aldehyde or ketone position.

"Halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

"Heterocycle" or "heterocyclic" refers to a carbocylic ring wherein one or more carbon atoms have been replaced with one or more heteroatoms such as nitrogen, oxygen or sulfur. A substitutable nitrogen on an aromatic or non-aromatic heterocyclic ring may be optionally substituted. The heteroatoms N or S may also exist in oxidized form such as NO, SO and $SO_2$. Examples of heterocycles include, but are not limited to, piperidine, pyrrolidine, morpholine, thiomorpholine, piperazine, tetrahydrofuran, tetrahydropyran, 2-pyrrolidinone, δ-valerolactam, δ-valerolactone and 2-ketopiperazine, among numerous others.

"Heteroatom-containing" refers to a molecule or molecular fragment in which one or more carbon atoms is replaced with an atom other carbon, e.g., nitrogen, oxygen, sulfur, phosphorus or silicon. "Substituted heterocycle" refers to a heterocycle as just described that contains one or more functional groups such as lower alkyl, acyl, aryl, cyano, halogen, hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like. In other instances where the term "substituted" is used, the substituents which fall under this definition may be readily gleaned from the other definitions of substituents that are presented in the specification as well the circumstances under which such substituents occur in a given chemical compound. One having ordinary skill in the art will recognize that the maximum number of heteroatoms in a stable, chemically feasible heterocyclic ring, whether it is aromatic or non-aromatic, is determined by the size of the ring, degree of unsaturation, and valence of the heteroatoms. In general, a heterocyclic ring may have one to four heteroatoms so long as the heterocyclic ring is chemically feasible and stable.

"Isostere" refers to compounds that have substantially similar physical properties as a result of having substantially similar electron arrangements.

"Substituted", as in "substituted alkyl" or "substituted alkenyl", means that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, amino, halo, silyl, and the like. When the term "substituted" appears prior to a list of possible substituted groups, it is intended that the term apply to every member of that group.

"Effective amount" refers to the amount of a selected compound, intermediate or reactant that is used to produce an intended result. The precise amount of a compound, intermediate or reactant used will vary depending upon the particular compound selected and its intended use, the age and weight of the subject, route of administration, and so forth, but may be easily determined by routine experimentation. In the case of the treatment of a condition or disease state, an effective amount is that amount which is used to effectively treat the particular condition or disease state.

The term "subjects" is used throughout the specification to describe an animal, preferably a human, to whom treatment, including prophylactic treatment, with the compositions according to the present invention is provided. For treatment of those infections, conditions or disease states which are specific for a specific animal such as a human patient, the term patient refers to that specific animal.

The present invention includes the pharmaceutically acceptable acid addition salts of compounds of formula (I). The acids that are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts.

The invention also includes base addition salts of formula (I). The chemical bases that may be used as reagents to prepare pharmaceutically acceptable base salts of those compounds of formula (I) that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e, calcium and magnesium), ammonium or water-soluble amine addition salts such as N-methylglucamine (meglumine), and the lower alkanolammonium and other base salts of pharmaceutically acceptable organic amines.

The compounds of this invention include all stereoisomers (i.e, cis and trans isomers) and all optical isomers of compounds of the formula (I) (e.g., R and S enantiomers), as well as racemic, diastereomeric and other mixtures of such isomers, as well as all polymorphs of the compounds.

As modulators of the GlyT2 receptor, the compounds of the instant invention are useful in an effective amount for treating central nervous system conditions in subjects suffering therefrom. Specific central nervous system conditions include conditions such as muscle spasticity, tinnitus, epilepsy and neuropathic pain.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and cornstarch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of a novel GlyT2 inhibitor of the instant invention that may be combined with the carrier materials to produce a single dosage form will vary depending upon the host treated and the particular mode of administration. Preferably, the compositions should be formulated to contain between about 10 milligrams to about 500 milligrams of active ingredient.

It should also be understood that a specific dosage and treatment regimen for any particular patient will depend upon a variety of factors, including the activity of the specific compound employed, the age, body weight, general health, sex, diet, time of administration, rate of excretion, drug combination, the judgment of the treating physician, and the severity of the particular disease or condition being treated.

General Synthetic Methods

Representative compounds of the present invention can be synthesized in accordance with the general synthetic methods described below and are illustrated more particularly in the schemes that follow. Since the schemes are illustrative, the invention should not be construed as being limited by the chemical reactions and conditions expressed. The preparation of the various starting materials used in the schemes is well within the skill of persons versed in the art.

Unless specified to the contrary, reactions herein occur at approximately atmospheric pressure and at a temperature of between about 0° C. and the boiling point of any organic solvent used in the reaction. Inert organic solvents such as dichloromethane, diethyl ether, dimethylformamide, chloroform or tetrahydrofuran are preferred solvents in the reactions disclosed herein. Reaction times can range from about one hour to about forty-eight hours, and reactants optionally are stirred, shaken, or agitated. Reactions can be done one pot or in steps, unless specified to the contrary.

As explained in detail hereinafter, in a purely illustrative embodiment, benzoylamine analogs of the invention of formula:

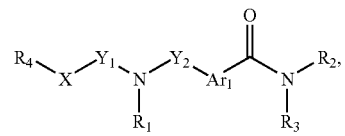

where $Y_2$ is methylene, may be synthesized by the reductive amination (A. F. Abdel-Magid et al., *J. Org. Chem.* 1996, 61:3849) of an amine of the formula:

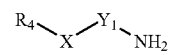

with an aldehyde of the formula:

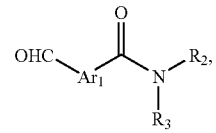

where the process is done in one pot or in steps, and where $R_4$, $X$, $Y_1$, $Ar_1$, $R_2$, and $R_3$ are as defined previously.

In a particular embodiment, benzoylamine analogs of the invention may be synthesized by the reductive amination of an amino adduct of the formula:

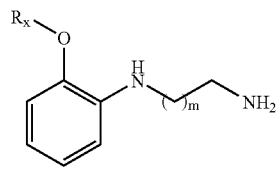

where $R_x$ can be, e.g., $C_{1-5}$alkyl and m is 1 or 2, with an aldehyde of the formula

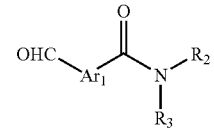

where $Ar_1$, $R_2$, and $R_3$ are as defined previously. Several alternative processes for making compounds of the invention are also described hereinafter.

The reductive amination reaction generally takes place under conditions that will be known to persons skilled in the art. For example, reductive amination can be achieved by the treatment of an aldehyde with an amine in the presence of a reducing agent in an inert solvent. Suitable reducing agents include borohydride reagents such as sodium borohydride. See Loudon, Organic Chemistry, Chp. 23, p. 1085 (Fourth Ed.) (Oxford University Press 2002).

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (W. C. Still et al., *J. Org. Chem.* 1978, 43:2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, diethyl ether, tetrahydrofuran and dioxane are common examples of an ethereal solvent; benzene, toluene, hexanes and cyclohexane are typical hydrocarbon solvents; and dichloromethane and dichloroethane are representative halohydrocarbon solvents. In those cases to the isopropyl ether (5b) upon treatment with isopropyl iodide in the presence of potassium carbonate in DMF. Condensation of 5b with either 2-chloroethylamine in refluxing isopropanol or with oxazolidinone in refluxing 2-(2-methoxyethoxy)ethanol provided the aminoethyl adduct 6a. Similarly, combining 5b with 3-chloropropylamine afforded the aminopropyl adduct 6b. Carbodiimide mediated coupling between piperidine and carboxylic acid (7) afforded aldehyde 8, which underwent reductive amination (A. F. Abdel-Magid, K. G. Carson, B. D. Harris, C. A. Maryanoff, D. Shah, *J. Org. Chem.* 1996, 61:3849) with either 6a or 6b in the presence of NaBH(OAc)$_3$/dichloroethane to provide adducts 4a and 4b respectively. Reagents used in Scheme 1 are: (a) Isopropyl iodide, K$_2$CO$_3$, DMF (b) 2-Chloroethylamine, i-PrOH, reflux (c) 3-Chloropropylamine, i-PrOH, reflux (d) 5b-HCl salt, oxazolidinone, 2-(2-methoxyethoxy)ethanol, 180° C. (e) Piperidine, EDCI, HOBT, DMF, Et$_3$N and (f) NaBH(OAc)$_3$, 1,2-dichloroethane.

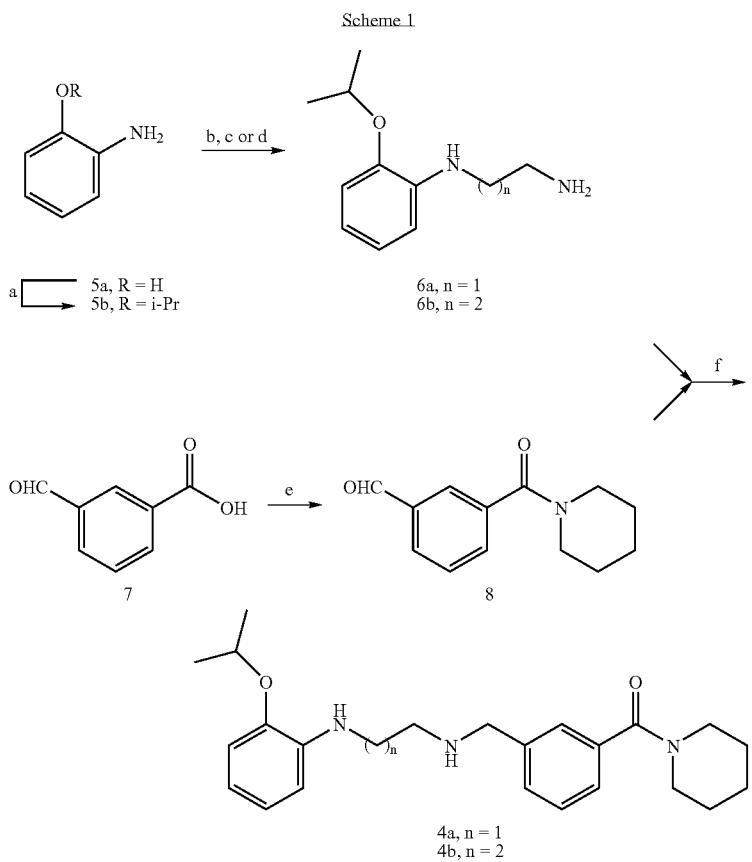

wherein the product is isolated as the acid addition salt, the free base may be obtained by techniques known to those skilled in the art. In those cases in which the product is isolated as an acid addition salt, the salt may contain one or more equivalents of the acid.

The following schemes illustrate the synthesis of the compounds of the present invention. The compound numbers used in the schemes do not correspond to the example numbers.

Reaction Scheme 1 illustrates two methods that were used to synthesize analogs of compound 4a of the instant invention. In reaction scheme 1, 2-aminophenol (5a) was converted In reaction Scheme 2, nitrophenols 9a and 9b were converted to anilines 10a-d utilizing the two-step sequence outlined (A. I. Meyers, L. Snyder, *J. Org. Chem.* 1993, 58:36; D. L. Boger, S. R. Duff, J. S. Panek, M. Yasuda, *J. Org. Chem.* 1985, 50:5782). Anilines 10e-g were obtained from commercial sources. Synthesis of the ethylenediamine analogs 12a-h was achieved as described in Scheme 1 for adducts 4a-b. Reagents employed in Scheme 2 are as follows: (a) R—Br, K$_2$CO$_3$, DMF (b) Na$_2$S$_2$O$_4$, THF—H$_2$O (c) H$_2$, Pd—C, EtOH (d) 10-HCl salt, oxazolidinone, 2-(2-methoxyethoxy)ethanol, 180° C. (e) 2-Chloroethylamine, i-PrOH, reflux and (f) compound 8, NaBH(OAc)$_3$, 1,2-dichloroethane.

Scheme 2

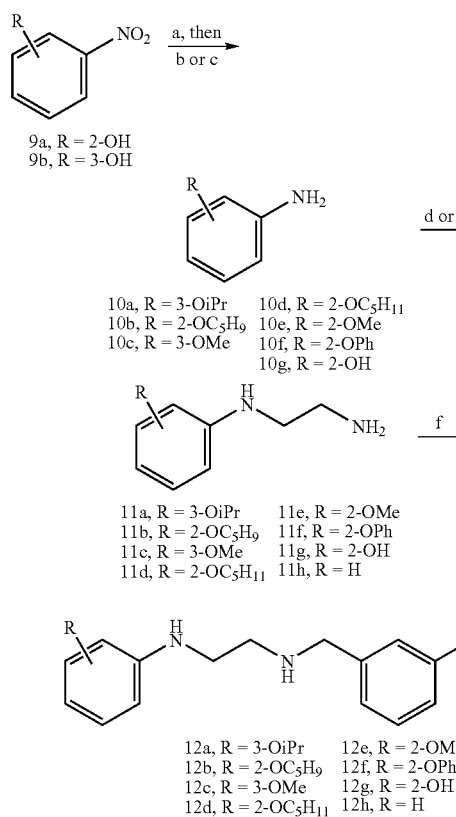

9a, R = 2-OH
9b, R = 3-OH

10a, R = 3-OiPr    10d, R = 2-OC$_5$H$_{11}$
10b, R = 2-OC$_5$H$_9$    10e, R = 2-OMe
10c, R = 3-OMe    10f, R = 2-OPh
                  10g, R = 2-OH

11a, R = 3-OiPr    11e, R = 2-OMe
11b, R = 2-OC$_5$H$_9$    11f, R = 2-OPh
11c, R = 3-OMe    11g, R = 2-OH
11d, R = 2-OC$_5$H$_{11}$    11h, R = H

12a, R = 3-OiPr    12e, R = 2-OMe
12b, R = 2-OC$_5$H$_9$    12f, R = 2-OPh
12c, R = 3-OMe    12g, R = 2-OH
12d, R = 2-OC$_5$H$_{11}$    12h, R = H

Substituted anilino derivatives 20a and 20b of the invention were synthesized as outlined in Scheme 3a. Condensation between 2-fluoronitrobenzene and ethylenediamine provided adduct 14, which underwent reductive amination with aldehyde 8 to afford intermediate 15. Selective protection of the benzylic nitrogen gave rise to carbamate 16, which was subjected to hydrogenation conditions to provide the anilino derivative 17, that was subsequently converted to compounds 20a and 20b. Reagents employed in Scheme 3a are as follows: (a) ethylenediamine or N-benzylethylenediamine, CH$_3$CN, heat (b) compound 8, NaBH(OAc)$_3$, 1,2-dichloroethane (c) (Boc)$_2$O, CH$_2$Cl$_2$ (d) H$_2$, Pd/C, EtOH, 1 h (e) Isopropyl iodide, K$_2$CO$_3$, DMF (f) appropriate sulfonyl chloride, Et$_3$N, CH$_2$Cl$_2$ and (h) TFA, CH$_2$Cl$_2$.

Scheme 3a

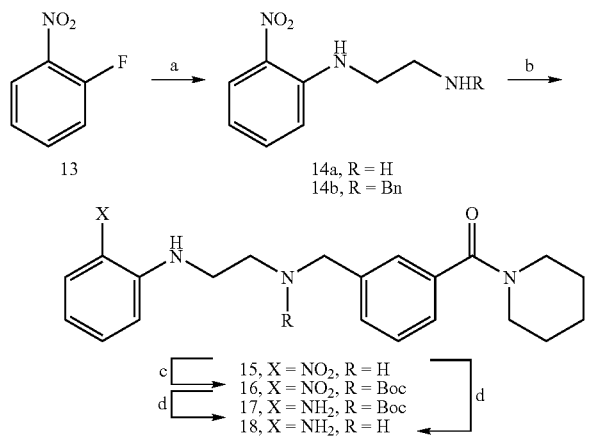

13

14a, R = H
14b, R = Bn

15, X = NO$_2$, R = H
16, X = NO$_2$, R = Boc
17, X = NH$_2$, R = Boc
18, X = NH$_2$, R = H

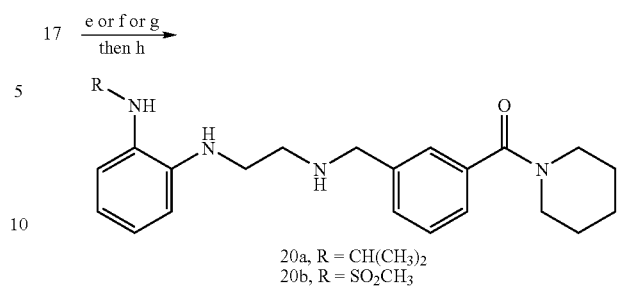

20a, R = CH(CH$_3$)$_2$
20b, R = SO$_2$CH$_3$

Urea derivatives 20c and 20d of the invention were synthesized as outlined in Scheme 3b. Reagents employed in Scheme 3b are as follows: (a) (Boc)$_2$O, CH$_2$Cl$_2$, (b) H$_2$, Pd/C, EtOH, 1 h, (c) Appropriate isocyanate, Et$_3$N, CH$_2$Cl$_2$ (d) TFA, CH$_2$Cl$_2$ (e) H$_2$, Pd/C, EtOH-HOAc (5:1, v/v), 50 psi, 24 h and (f) compound 8, NaB(OAc)$_3$H, 1,2-dichloroethane.

Scheme 3b

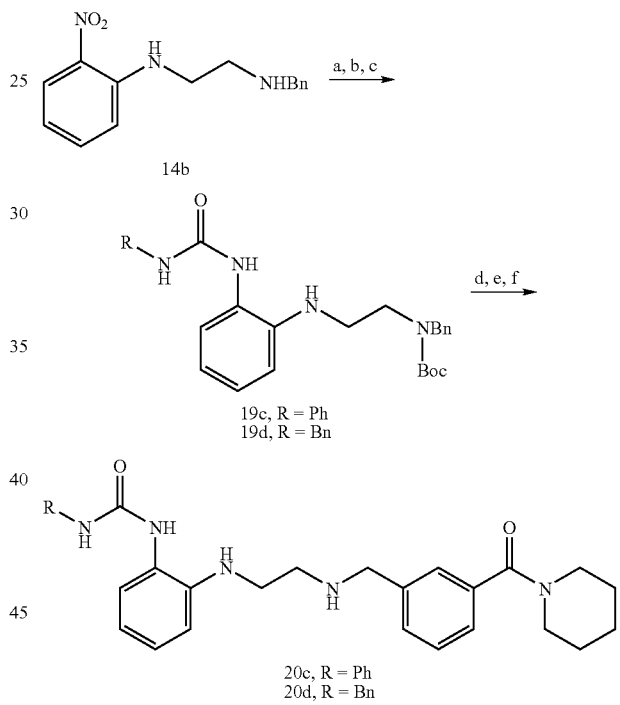

14b

19c, R = Ph
19d, R = Bn

20c, R = Ph
20d, R = Bn

Halogenated analogs 23a-d of the invention were prepared from the commercially available haloanilines 21a-d as depicted in reaction Scheme 4. Reagents employed in Scheme 4 are as follows: (a) 2-Chloroethylamine, i-PrOH, reflux and (b) compound 8, NaBH(OAc)$_3$, 1,2-dichloroethane.

Scheme 4

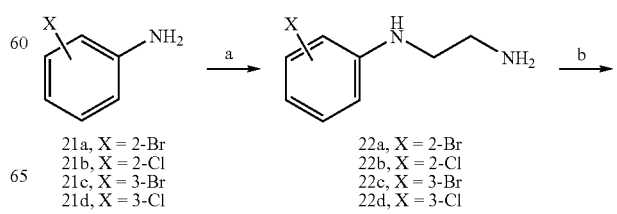

21a, X = 2-Br
21b, X = 2-Cl
21c, X = 3-Br
21d, X = 3-Cl

22a, X = 2-Br
22b, X = 2-Cl
22c, X = 3-Br
22d, X = 3-Cl

-continued

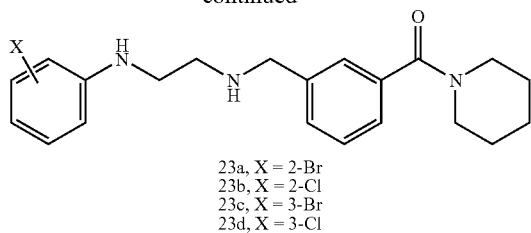

23a, X = 2-Br
23b, X = 2-Cl
23c, X = 3-Br
23d, X = 3-Cl

As shown in Scheme 5, 2-thienyl, 2-naphthyl and 2-methoxyphenyl analogs 28a-c of the invention were assembled via Suzuki coupling between bromide 24 and the requisite boronic acid. The 2-isopropyl analog 28d was obtained starting from 2-(isopropylamino)phenol (25). Reagents employed in Scheme 5 are as follows: (a) 2-Chloroethylamine, i-PrOH, reflux (b) compound 8, NaBH(OAc)$_3$, 1,2-dichloroethane and (c) appropriate arylboronic acid, Pd(PPh$_3$)$_4$, EtOH-Toluene (1:4 v/v), Na$_2$CO$_3$, reflux.

Scheme 5

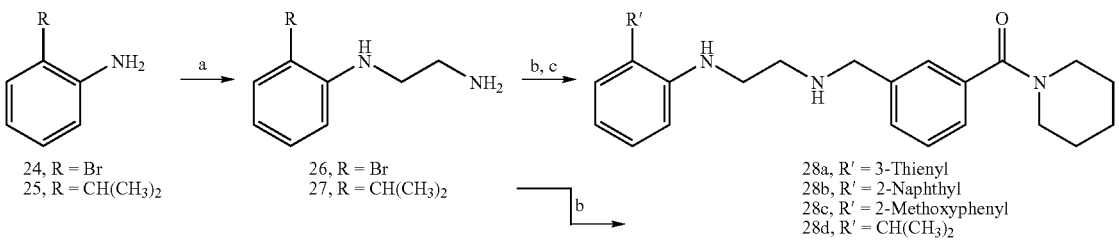

24, R = Br
25, R = CH(CH$_3$)$_2$

26, R = Br
27, R = CH(CH$_3$)$_2$

28a, R' = 3-Thienyl
28b, R' = 2-Naphthyl
28c, R' = 2-Methoxyphenyl
28d, R' = CH(CH$_3$)$_2$ As illustrated in reaction Scheme 6, treatment of 2-(isopropoxy)phenol (29) with NaH in THF followed by N-(3-bromopropyl)phthamide provided the adduct 30. Hydrolysis of the phthalimide moiety with hydrazine, followed by reductive amination with 8 afforded the oxygen analog 31. Coupling of 29 with N-t-Boc-ethanolamine under Mitsunobu conditions provided adduct 31. Subsequent deprotection with TFA in CH$_2$Cl$_2$ and treatment with 8 and NaBH(OAc)$_3$ afforded the ether derivative 33. Reagents employed in Scheme 6 are as follows: (a) N-(3-Bromopropyl)phthalimide, K$_2$CO$_3$, DMF (b) NH$_2$NH$_2$, EtOH (c) compound 8, NaBH(OAc)$_3$, 1,2-dichloroethane (d) N-t-Boc-Ethanolamine, DBAD, Ph$_3$P, THF and (e) CF$_3$CO$_2$H, CH$_2$Cl$_2$.

Scheme 6

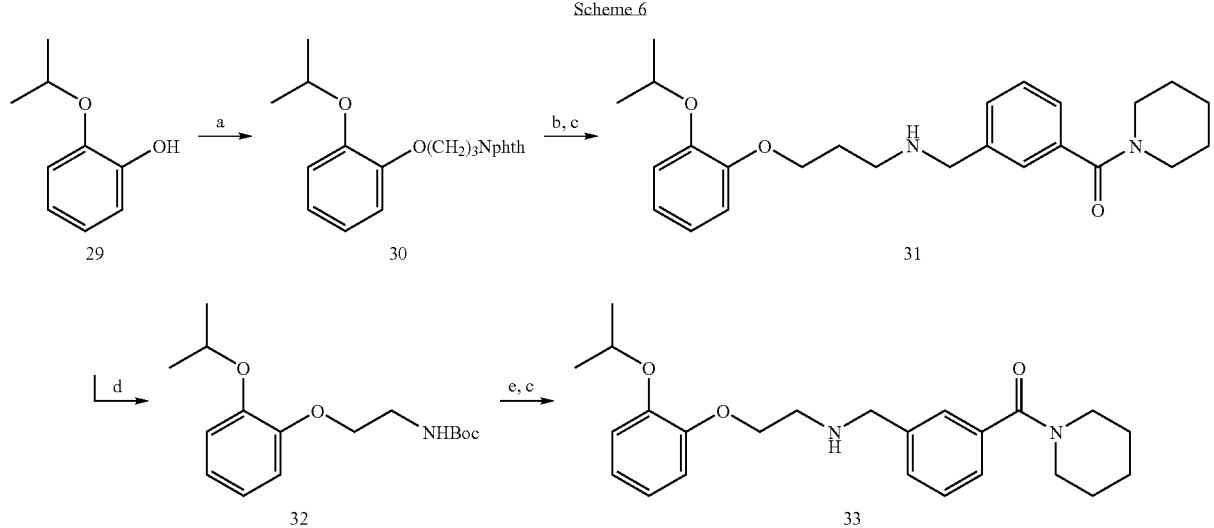

As illustrated in reaction Scheme 7, compound 33 was coupled with N-t-Boc-ethanolamine under Mitsunobu conditions to give adduct 33b, which upon treatment with TFA provided the primary amine 33c. Subsequent condensation with aldehyde 8 under reductive amination conditions afforded compound 34. Hydrolysis of the benzoate ester, followed by alkylation of the phenol with isopropyl iodide provided compound 36. Reagents employed in Scheme 7 are as follows: (a) N-t-Boc-Ethanolamine, DBAD, Ph$_3$P, THF (b) CF$_3$CO$_2$H, CH$_2$Cl$_2$ (c) compound 8, NaBH(OAc)$_3$, 1,2-dichloroethane (d) NaOH, THF—H$_2$O and (e) 2-iodopropane, K$_2$CO$_3$, DMF.

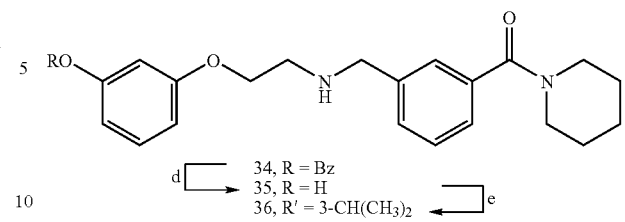

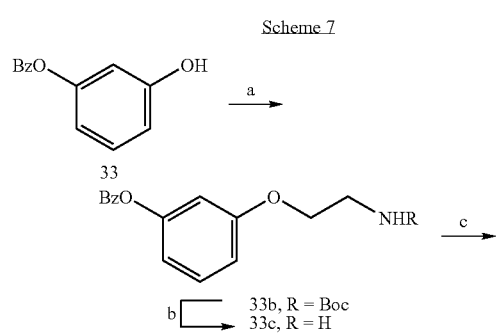

As illustrated in reaction Scheme 8, 4a was selectively methylated at the benzylic nitrogen using K$_2$CO$_3$ and MeI in DMF to afford 39. Accessing the mono N-methyl derivative 42 first required N-Boc protection of the more reactive benzylic nitrogen. The resulting carbamate 40 was then treated with NaH and MeI in DMF to afford intermediate 41. Deprotection of 41 with TFA gave rise to 42. The dialkylated analog 43 was obtained by subjecting 42 to the above methylation conditions as illustrated in reaction Scheme 8. Reagents employed in Scheme 8 are as follows: (a) K$_2$CO$_3$, DMF, MeI (b) (Boc)$_2$O, CH$_2$Cl$_2$ (c) CF$_3$CO$_2$H, CH$_2$Cl$_2$ and (d) NaH, DMF, MeI.

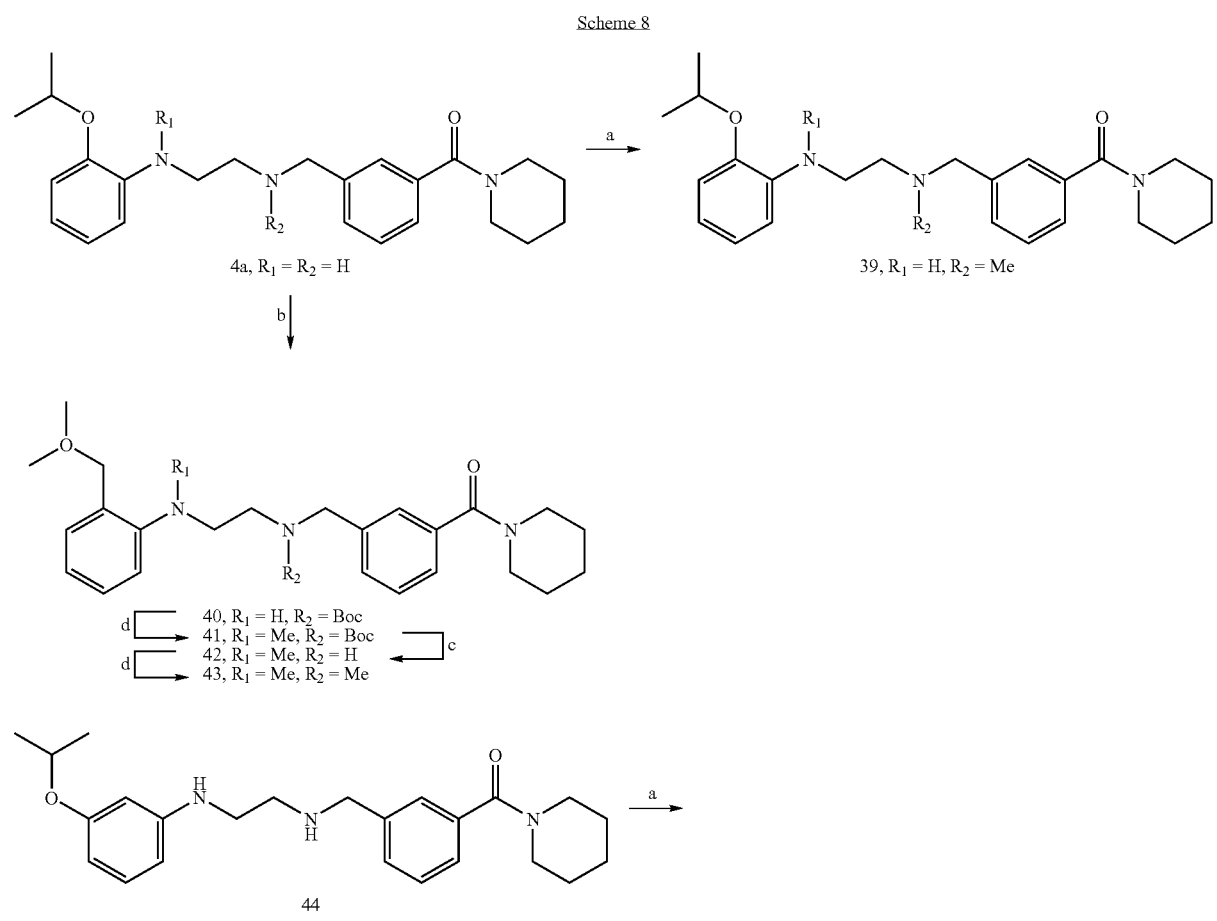

-continued

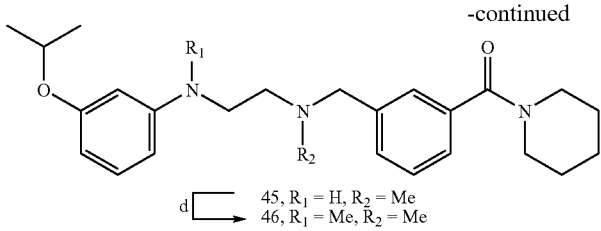

45, $R_1$ = H, $R_2$ = Me
46, $R_1$ = Me, $R_2$ = Me

As illustrated in reaction Scheme 9, the anilino nitrogen of 4a may be replaced with sulfur. Sequential alkylation of thiophenol 47, first with N-(2-bromoethyl)phthalimide, and then with 2-iodopropane, produced compound 48. The phthalimide moiety was removed with hydrazine, and the resulting amine was condensed with 8 to provide the sulfur isostere 49. Reagents employed in scheme 9 are as follows: (a) N-(2-Bromoethyl)phthalimide, $K_2CO_3$, DMF (b) 2-Iodopropane, $K_2CO_3$, DMF (c) $NH_2NH_2$, EtOH and (d) compound 8, $NaBH(OAc)_3$, 1,2-dichloroethane.

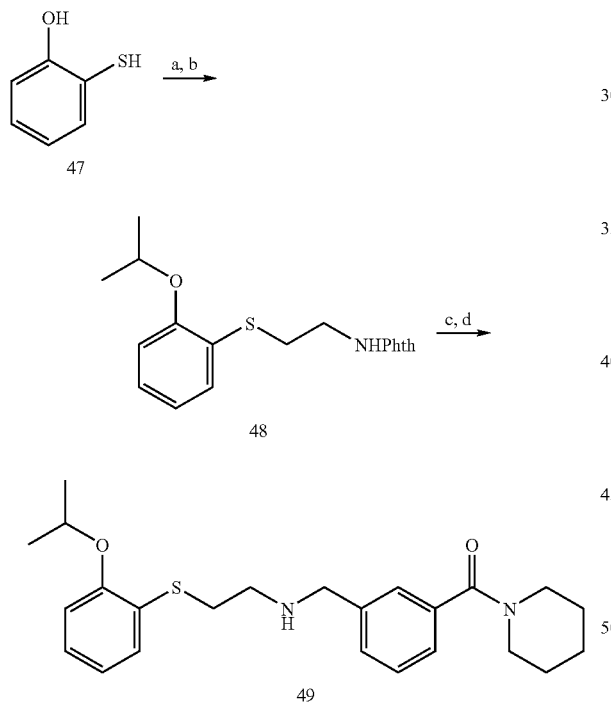

Carbon isosteres of the invention were prepared as shown in reaction Scheme 10. Treatment of 3-(2-hydroxyphenyl) propionic acid 50 with $K_2CO_3$ and 2-iodopropane provided the diisopropyl adduct 51a. Treatment of 51a with methanolic ammonia gave rise to the corresponding amide 51b, which was reduced with $LiAlH_4$ to afford the amine 52. Reductive amination with 8 gave congener 53. Reagents employed in Scheme 10 are as follows: (a) 2-Iodopropane, $K_2CO_3$, DMF, (b) $NH_3$-MeOH (c) LAH, THF and (d) compound 8, $NaBH(OAc)_3$, 1,2-dichloroethane.

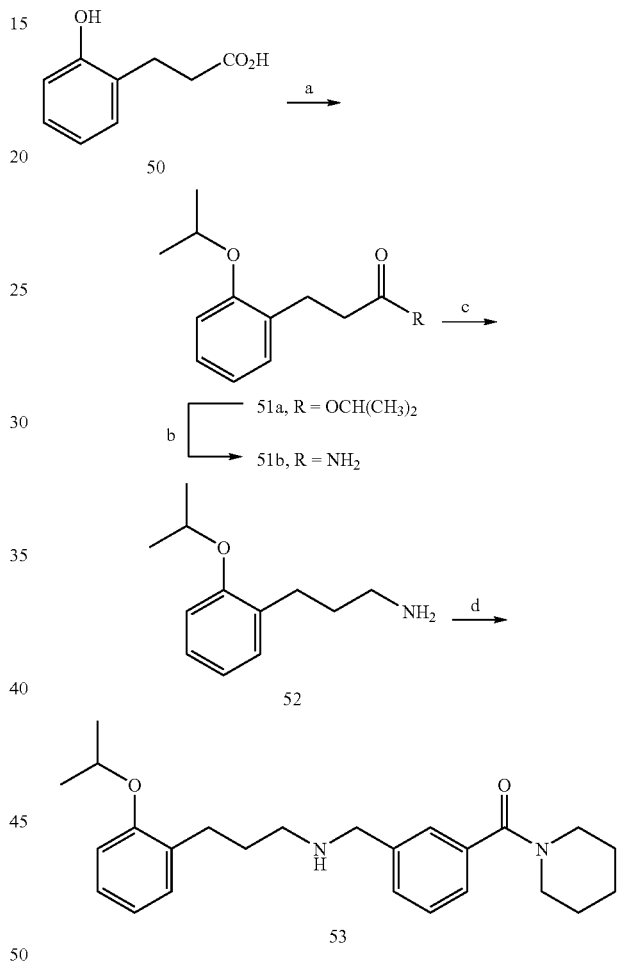

As outlined in reaction Scheme 11, carbodiimide mediated coupling of commercially available compound 54 with piperidine afforded the thiophene-2-carboxaldehyde 55. Reductive amination with 6a afforded the thiophene isostere 56. The aniline derivatives 60 and 62 were accessed by way of intermediate 55, which was coupled with amine 14 to provide compound 57. Following protection of the benzylic nitrogen and reduction of the nitro group, the resulting aniline 59 underwent alkylation with 2-iodopropane to afford compound 61. Removal of the Boc group produced the desired isostere 62. Reagents employed in Scheme 11 are as follows: (a) Piperidine, DMF, HOBT, EDCI (b) $NaBH(OAc)_3$, 1,2-dichloroethane (c) $(Boc)_2O$, $Et_3N$, $CH_2Cl_2$ (d) $H_2$, Pd/C, EtOH (e) 2-Iodopropane, $K_2CO_3$, DMF and (f) HCl-Dioxane, $CH_2Cl_2$.

Scheme 11

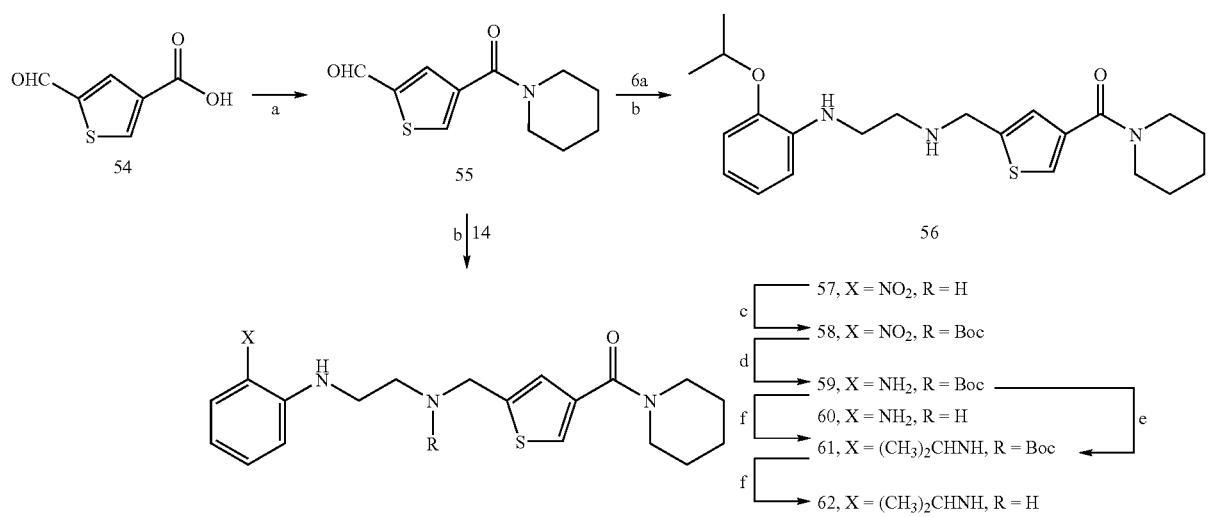

GlyT2 antagonist activity of representative compounds of the invention was determined in accordance with the assay described in the Examples and by measuring the ability of compounds to inhibit the uptake of [$^{14}$C]-glycine in COS-7 cells transfected with the human glycine transporter-2 (GlyT2). The GlyT2 antagonist activities of these representative compounds are set forth hereinafter in Table 1.

The following examples describe the invention in greater detail and are intended to illustrate the invention, but not to limit it. All compounds were identified by a variety of methods including nuclear magnetic resonance spectroscopy, mass spectrometry and, in some cases, infrared spectroscopy and elemental analysis. Unless otherwise noted, the materials used in the examples were obtained from readily available commercial sources or synthesized by standard methods known to those skilled in the art.

EXAMPLES

General Experimental Details

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration). $^{13}$C NMR data is shown in ppm.

Mass spectra were obtained on an Agilent series 1100 MSD using electrospray ionization (ESI) in either positive or negative mode as indicated. The "mass calculated" for a molecular formula is the monoisotopic mass of the compound.

Flash column chromatography was accomplished using the ISCO Foxy 200 system and one of the following commercially-available, prepacked columns: Biotage 40S (SiO$_2$; 40 g), Biotage 40M (SiO$_2$; 90 g), Biotage 40L (SiO$_2$; 120 g), Biotage 65M (SiO$_2$; 300 g) or ISCO Redisep (SiO$_2$; 10, 12, 35, 40, or 120 g).

Preparative TLC was accomplished using PLC plates (20× 20 cm silica gel 60 F$_{254}$, 0.5 mm).

Example 1

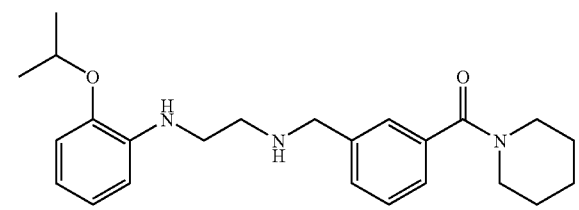

(3-{[2-(2-Isopropoxy-phenylamino)-ethylamino]-methyl}-phenyl)-piperidin-1-yl-methanone A. 1-Isopropoxy-2-nitro-benzene. To a solution of 2-nitrophenol (0.14 g, 1.0 mmol) in DMF (2 mL) was added K$_2$CO$_3$ (0.69 g, 5.0 mmol), and the resulting suspension was stirred for 15 min. 2-Iodopropane (0.34 g, 2.0 mmol) was added. The reaction mixture was stirred at 25° C. overnight, then was diluted with ethyl acetate (EtOAc, 20 mL), and washed with H$_2$O (10 mL), 1 N NaOH (2×20 mL), satd NaHCO$_3$ (2×20 mL) and then brine (20 mL). The organic layer was dried (Na$_2$SO$_4$), filtered, and concentrated under reduced pressure to provide a yellow oil (0.141 g, 77%). $^1$H NMR (400 MHz, CDCl$_3$): 7.76 (dd, J=8.0, 1.5 Hz, 1H), 7.48 (dt, J=8.7, 1.6 Hz, 1H), 7.07 (d, J=8.4 Hz, 1H), 6.98 (t, J=8.2 Hz, 1H), 4.67 (hept, J=6.1 Hz, 1H), 1.39 (d, J=6.1 Hz, 6H).

B. 2-Isopropoxy-phenylamine. To a solution of 1-isopropoxy-2-nitro-benzene (10 g, 55 mmol) in THF (100 mL) was added a solution of sodium hydrosulfite (48 g, 280 mmol) in H$_2$O (200 mL). The reaction mixture was stirred at 25° C. for 1 h then at 55° C. for 2 h. The mixture was treated with 1 N HCl (50 mL), followed by 1 N NaOH (50 mL) to neutralize the solution, and then was extracted with EtOAc (3×100 mL). The combined organic layers were washed with brine, dried (MgSO$_4$), filtered, and concentrated under reduced pressure. The crude residue was purified by column chromatography (CH₂Cl₂) to provide a tan oil (2.2 g, 26%). MS (ESI): mass calculated for C₉H₁₃NO, 151.10; m/z found, 152.1 [M+H]⁺. ¹H NMR (400 MHz, CDCl₃): 6.81-6.68 (m, 4H), 4.52 (hept, J=6.1 Hz, 1H), 3.64 (br s, 2H), 1.35 (d, J=6.1 Hz, 6H).

C. N¹-(2-Isopropoxy-phenyl)-ethane-1,2-diamine. To a solution of 2-isopropoxy-phenylamine (2.18 g, 14.4 mmol) in isopropanol (20 mL) was added 2-chloroethylamine hydrochloride (2.3 g, 20 mmol), and the mixture was stirred at 85° C. for 24 h. Triethylamine (1.46 g, 14.4 mmol) was added, and the resulting mixture was stirred at 85° C. for 24 h. The reaction mixture was made basic using 1 N NaOH (40 mL), and the aqueous layer was extracted with EtOAc (3×100 mL). The combined organic layers were washed with brine, dried (MgSO₄), filtered, and concentrated under reduced pressure. The crude residue was purified by column chromatography (1:10:150 NH₄OH/CH₃OH/CH₂Cl₂, then with 10% CH₃OH/CH₂Cl₂) to give a brown oil (0.59 g, 21%). MS (ESI): mass calculated for C₁₁H₁₈N₂O, 194.14; m/z found, 195.1 [M+H]⁺. ¹H NMR (400 MHz, CDCl₃): 6.84 (dt, J=7.6, 1.4 Hz, 1H), 6.77 (dd, J=8.0, 1.4 Hz, 1H), 6.65-6.61 (m, 2H), 4.52 (hept, J=6.1 Hz, 1H), 3.22 (t, J=5.8 Hz, 2H), 2.94 (t, J=6.0 Hz, 2H), 1.61 (br s, 2H), 1.35 (d, J=6.1 Hz, 6H). ¹³C NMR (100 MHz, CDCl₃): 144.9, 139.2, 121.2, 116.4, 112.5, 110.2, 70.6, 46.5, 41.2, 22.3.

D. 3-(Piperidine-1-carbonyl)-benzaldehyde. To a solution of 3-formyl-benzoic acid (2.0 g, 13 mmol) in DMF (130 mL) was added piperidine (1.25 g, 14.7 mmol), and the resulting solution was stirred at 25° C. for 15 min. The solution was treated with HOBt (2.7 g, 20 mmol) and EDCI (3.8 g, 20 mmol), and the reaction mixture was stirred at 25° C. for 18 h. The mixture was partitioned with H₂O (250 mL) and EtOAc (300 mL), and the organic layer was washed with 1 M NaOH (100 mL), 1 M HCl (100 mL) then brine (100 mL), dried (Na₂SO₄), filtered, and concentrated under reduced pressure to provide a colorless oil (2.21 g, 76%). MS (ESI): mass calculated for C₁₃H₁₅NO₂, 217.11; m/z found, 218.1 [M+H]⁺. ¹H NMR (400 MHz, CDCl₃): 10.04 (s, 1H), 7.94-7.90 (m, 2H), 7.68-7.57 (m, 2H), 3.73 (br s, 2H), 3.34 (br s, 2H), 1.70-1.54 (m, 6H).

E. (3-{[2-(2-Isopropoxy-phenylamino)-ethylamino]-methyl}-phenyl)-piperidin-1-yl-methanone. To a solution of N¹-(2-isopropoxy-phenyl)-ethane-1,2-diamine (0.228 g, 1.17 mmol) in 1,2-dichloroethane (2.8 mL) was added a solution of 3-(piperidine-1-carbonyl)-benzaldehyde (0.213 g, 0.980 mmol), and the mixture was stirred at 25° C. for 15 min. The mixture was treated with NaBH(OAc)₃ (0.311 g, 1.47 mmol), and the resulting suspension was stirred at 25° C. for 5 h. The suspension was partitioned with 1 M NaOH (25 mL) and EtOAc (50 mL), and the organic layer was washed with brine (25 mL), dried (Na₂SO₄), filtered, and concentrated under reduced pressure. The crude residue was purified by column chromatography (0-5% CH₃OH/CH₂Cl₂) to provide the desired product as a colorless oil (0.256 g, 66%). MS (ESI): mass calculated for C₂₄H₃₃N₃O₂, 395.26; m/z found, 396.3 [M+H]⁺, 418.3 [M+Na]⁺. ¹H NMR (400 MHz, CDCl₃): 7.40-7.23 (m, 4H), 6.85-6.76 (m, 2H), 6.65-6.60 (m, 2H), 4.51 (hept, J=6.1 Hz, 1H), 3.84 (s, 3H), 3.69 (br s, 2H), 3.31 (br s, 2H), 3.27 (t, J=5.9 Hz, 2H), 2.91 (t, J=6.0 Hz, 2H), 1.66-1.49 (br m, 6H), 1.35 (d, J=6.1 Hz, 6H). ¹³C NMR (100 MHz, CDCl₃): 170.2, 145.0, 140.4, 139.3, 136.6, 129.0, 128.4, 126.4, 125.3, 121.2, 116.4, 112.5, 110.3, 53.2, 48.7, 48.1, 43.3, 43.0, 26.5, 25.6, 24.5, 22.3.

Example 2

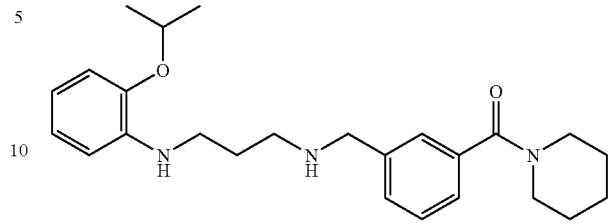

(3-{[3-(2-Isopropoxy-phenylamino)-propylamino]-methyl}-phenyl)-piperidin-1-yl-methanone A. N¹-(2-Isopropoxy-phenyl)-propane-1,3-diamine. To a solution of 2-isopropoxy-phenylamine (0.50 g, 3.3 mmol) in isopropanol (7 mL) was added Et₃N (0.67 g, 6.6 mmol) and 3-chloropropylamine hydrochloride (0.515 g, 3.96 mmol). The reaction mixture was heated to 50° C. for 24 h, then to 90° C. for 24 h. The mixture was treated with satd NaHCO₃ (20 mL), EtOAc (40 mL) and H₂O (20 mL), and then the aqueous layer was back-extracted with EtOAc (3×40 mL). The combined organic layers were washed with brine, dried (MgSO₄), filtered, and concentrated under reduced pressure. The resulting residue was purified by column chromatography (50-100% EtOAc/hexanes) to provide an amber oil (0.10 g, 15%). MS (ESI): mass calculated for C₁₂H₂₀N₂O, 208.16; m/z found, 209.1 [M+H]⁺. ¹H NMR (400 MHz, CDCl₃): 6.85-6.81 (m, 1H), 6.77-6.60 (m, 1H), 6.66-6.60 (m, 2H), 4.51 (hept, J=6.1 Hz, 1H), 3.27 (t, J=6.6 Hz, 2H), 3.10 (t, J=7.0 Hz, 2H), 2.06 (quint, J=6.7 Hz, 2H), 1.34 (d, J=6.1 Hz, 6H).

B. (3-{[3-(2-Isopropoxy-phenylamino)-propylamino]-methyl}-phenyl)-piperidin-1-yl-methanone. The title compound was prepared as in Example 1, steps D and E, substituting N¹-(2-isopropoxy-phenyl)-propane-1,3-diamine for N¹-(2-isopropoxy-phenyl)-ethane-1,2-diamine in step E. MS (ESI): mass calculated for C₂₅H₃₅N₃O₂, 409.27; m/z found, 410.3 [M+H]⁺. ¹H NMR (400 MHz, CDCl₃): 7.37-7.32 (m, 3H), 7.26-7.22 (m, 1H), 6.87-6.82 (m, 1H), 6.78-6.76 (m, 1H), 6.64-6.60 (m, 2H), 4.54-4.45 (m, 1H), 3.84 (br s, 2H), 3.71 (br s, 2H), 3.32 (br s, 2H), 3.21 (t, J=6.7 Hz, 2H), 2.78 (t, J=6.8 Hz, 2H), 1.90-1.84 (m, 2H), 1.67 (br s, 4H), 1.51 (br s, 2H), 1.33 (d, J=6.1 Hz, 6H).

Example 3

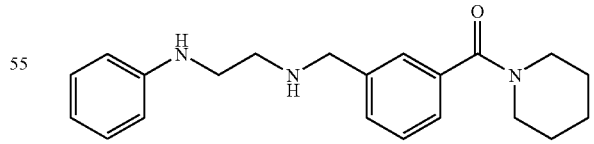

{3-[(2-Phenylamino-ethylamino)-methyl]-phenyl}-piperidin-1-yl-methanone

The title compound was prepared as in Example 1, steps D and E, substituting N¹-phenylethane-1,2-diamine for N¹-(2-isopropoxy-phenyl)-ethane-1,2-diamine in step E. ¹H NMR (400 MHz, CDCl₃): 7.38-7.32 (m, 3H), 7.26-7.25 (m, 1H), 7.19-7.14 (m, 2H), 6.70 (t, J=7.4 Hz, 1H), 6.63 (d, J=7.7 Hz, 2H), 3.85 (s, 2H), 3.70 (br s, 2H), 3.31 (br s, 2H), 3.25 (t, J=5.7 Hz, 2H), 2.93 (t, J=5.7 Hz, 2H), 1.67 (br s, 4H), 1.50 (br s, 2H), 1.26 (br s, 2H).

Example 4

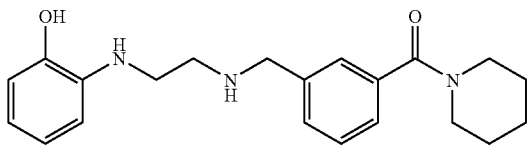

(3-{[2-(2-Hydroxy-phenylamino)-ethylamino]-methyl}-phenyl)-piperidin-1-yl-methanone The title compound was prepared as in Example 1, steps C-E, substituting 2-aminophenol for 2-isopropoxy-phenylamine in Step C.

A. 2-(2-Amino-ethylamino)-phenol. MS (ESI): mass calculated for $C_8H_{12}N_2O$, 152.09; m/z found, 153.1 [M+H]$^+$. $^1$H NMR (400 MHz, D$_2$O): 6.77-6.71 (m, 2H), 6.64-6.57 (m, 2H), 3.31 (t, J=6.1 Hz, 2H), 3.05 (t, J=6.0 Hz, 2H). $^1$H NMR (400 MHz, DMSO-d$_6$): 9.35 (br s, 1H), 8.21 (br s, 2H), 6.72 (dd, J=7.7, 1.3 Hz, 1H), 6.63 (dt, J=7.7, 1.3 Hz, 1H), 6.55 (dd, J=7.8, 1.3 Hz, 1H), 6.44 (dt, J=7.5, 1.4 Hz, 1H). $^{13}$C NMR (100 MHz, D$_2$O): 144.5, 136.3, 121.7, 119.3, 115.3, 112.8, 41.0, 38.8.

B. (3-{[2-(2-Hydroxy-phenylamino)-ethylamino]-methyl}-phenyl)-piperidin-1-yl-methanone. MS (ESI): mass calculated for $C_{21}H_{27}N_3O_2$, 353.21; m/z found, 354.1 [M+H]$^+$, 376.1 [M+Na]$^+$. $^1$H NMR (400 MHz, CDCl$_3$): 7.33-7.21 (m, 4H), 6.74-6.70 (m, 1H), 6.62-6.50 (m, 3H), 3.79 (s, 3H), 3.69 (br s, 2H), 3.28 (br s, 2H), 3.21 (t, J=5.3 Hz, 2H), 2.82 (t, J=5.5 Hz, 2H), 1.64 (br s, 4H), 1.45 (br s, 2H). $^{13}$C NMR (100 MHz, CDCl$_3$): 170.4, 145.3, 139.6, 137.4, 136.2, 129.5, 128.4, 126.7, 125.4, 120.3, 117.9, 114.8, 112.5, 52.9, 48.7, 47.7, 43.9, 43.2, 26.4, 25.5, 24.4.

Example 5

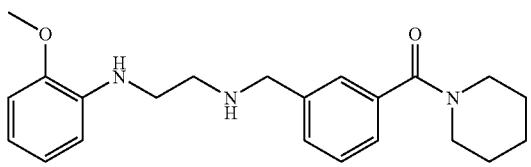

(3-{[2-(2-Methoxy-phenylamino)-ethylamino]-methyl}-phenyl)-piperidin-1-yl-methanone The title compound was prepared as in Example 1, steps C-E, substituting 2-methoxy-phenylamine for 2-isopropoxy-phenylamine in step C.

A. N$^1$-(2-Methoxy-phenyl)-ethane-1,2-diamine. MS (ESI): mass calculated for $C_9H_{14}N_2O$, 166.11, m/z found, 167.1 [M+H]$^+$. $^1$H NMR (400 MHz, CDCl$_3$): 8.17 (br s, 2H), 6.83-6.76 (m, 2H), 6.62-6.56 (m, 2H), 5.19 (br t, J=4.3 Hz, 1H), 3.76 (s, 3H), 3.37-3.32 (m, 2H), 2.95 (t, J=4.8 Hz, 2H). $^{13}$C NMR (100 MHz, DMSO-d$_6$): 146.6, 137.3, 121.0, 116.2, 110.0, 109.2, 55.3, 37.7.

B. (3-{[2-(2-Methoxy-phenylamino)-ethylamino]-methyl}-phenyl)-piperidin-1-yl-methanone. MS (ESI): mass calculated for $C_{22}H_{29}N_3O_2$, 367.23; m/z found, 368.3 [M+H]$^+$, 390.2 [M+Na]$^+$. $^1$H NMR (400 MHz, CDCl$_3$): 7.38-7.31 (m, 3H), 7.26-7.23 (m, 1H), 6.85 (dt, J=7.6, 1.3 Hz, 1H), 6.75 (dd, J=7.9, 1.3 Hz, 1H), 6.65 (dt, J=7.6, 1.4 Hz, 1H), 6.61 (d, J=7.8 Hz, 2H), 3.85-3.81 (m, 5H), 3.69 (br s, 2H), 3.31 (br s, 2H), 3.26 (t, J=5.8 Hz, 2H), 2.91 (t, J=6.0 Hz, 2H), 1.65 (br s, 4H), 1.49 (br s, 2H). $^{13}$C NMR (100 MHz, CDCl$_3$): 170.1, 146.8, 140.2, 138.1, 136.5, 129.0, 128.3, 126.3, 125.3, 121.1, 116.4, 109.8, 109.3, 55.3, 53.1, 48.6, 47.9, 43.1, 43.0, 26.4, 25.5, 24.4.

Example 6

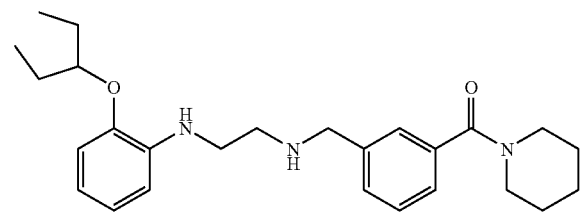

[3-({2-[2-(1-Ethyl-propoxy)-phenylamino]-ethylamino}-methyl)-phenyl]-piperidin-1-yl-methanone The title compound was prepared as in Example 1, steps A-E substituting 3-iodopentane for 2-iodopropane in step A.

A. 1-(1-Ethyl-propoxy)-2-nitro-benzene. $^1$H NMR (400 MHz, CDCl$_3$): 7.77 (dd, J=5.1, 1.7 Hz, 1H), 7.50-7.46 (m, 1H), 7.08-7.06 (m, 1H), 6.99-6.94 (m, 1H), 4.92-4.88 (m, 1H), 1.94-1.90 (m, 4H), 1.87-1.81 (m, 2H), 1.65-1.62 (m, 2H). $^{13}$C NMR (100 MHz, CDCl$_3$): 151.4, 133.6, 125.4, 119.6, 115.5, 81.3, 32.7, 23.8.

B. 2-(1-Ethyl-propoxy)-phenylamine. MS (ESI): mass calculated for $C_{11}H_{17}NO$, 179.13, m/z found, 180.1 [M+H]$^+$. $^1$H NMR (400 MHz, CDCl$_3$): 6.78-6.66 (m, 4H), 4.12 (quint, J=5.8 Hz, 1H), 3.55 (br s, 2H), 1.73-1.66 (m, 4H), 0.96 (t, J=7.5 Hz, 6H). $^{13}$C NMR (100 MHz, CDCl$_3$): 145.9, 137.1, 120.8, 118.3, 115.2, 113.2, 80.5, 26.1, 9.6.

C. N$^1$-[2-(1-Ethyl-propoxy)-phenyl]-ethane-1,2-diamine. MS (ESI): mass calculated for $C_{13}H_{22}N_2O$, 222.17; m/z found, 223.3 [M+H]$^+$.

D. [3-({2-[2-(1-Ethyl-propoxy)-phenylamino]-ethylamino}-methyl)-phenyl]-piperidin-1-yl-methanone. MS (ESI): mass calculated for $C_{26}H_{37}N_3O_2$, 423.29, m/z found, 424.5 [M+H]$^+$, 446.5 [M+Na]$^+$. $^1$H NMR (400 MHz, CDCl$_3$): 7.40-7.39 (m, 1H), 7.34-7.31 (m, 2H), 7.26-7.24 (m, 1H), 6.85-6.81 (m, 1H), 6.76-6.74 (m, 1H), 6.64-6.60 (m, 2H), 4.12 (quint, J=5.8 Hz, 1H), 3.85 (br s, 2H), 3.70 (br s, 2H), 3.30-3.27 (m, 4H), 2.94 (t, J=5.9 Hz, 2H), 1.73-1.66 (m, 8H), 1.49 (br s, 2H), 0.95 (t, J=7.4 Hz, 6H). $^{13}$C NMR (100 MHz, CDCl$_3$): 170.2, 145.5, 140.3, 139.2, 136.6, 129.0, 128.4, 126.4, 125.3, 121.0, 116.3, 112.2, 110.2, 80.6, 53.2, 48.7, 48.0, 43.2, 43.1, 26.4, 26.1, 25.6, 24.5, 9.6.

Example 7

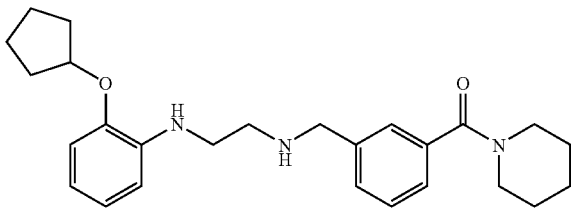

(3-{[2-(2-Cyclopentyloxy-phenylamino)-ethylamino]-methyl}-phenyl)-piperidin-1-yl-methanone The title compound was prepared as in Example 1, steps A-E substituting iodocyclopentane for 2-iodopropane in step A.

A. 1-Cyclopentyloxy-2-nitro-benzene. $^1$H NMR (400 MHz, CDCl$_3$): 7.77 (dd, J=8.7, 1.7 Hz, 1H), 7.50-7.46 (m, 1H), 7.08-7.06 (m, 1H), 6.99-6.94 (m, 1H), 4.92-4.88 (m, 1H), 1.94-1.90 (m, 4H), 1.87-1.81 (m, 2H), 1.65-1.62 (m, 2H).

B. 2-Cyclopentyloxy-phenylamine. To a solution of 1-cyclopentyloxy-2-nitro-benzene (5.0 g, 24 mmol) in ethanol (EtOH, 95 mL) was added Pd on carbon (Pd/C; 10 wt %, 5.14 g), and the resulting suspension was stirred under H$_2$ (50 psi) at 25° C. for 6 h. The suspension was filtered (diatomaceous earth), and the filtrate was concentrated under reduced pressure. The crude residue was purified by column chromatography (5-10% EtOAc/hexanes) to provide the desired product (3.6 g, 84%). MS (ESI): mass calculated for C$_{11}$H$_{15}$NO, 177.12; m/z found, 178.1 [M+H]$^+$. $^1$H NMR (400 MHz, CDCl$_3$): 6.80-6.68 (m, 4H), 4.80-4.76 (m, 1H), 1.94-1.85 (m, 4H), 1.83-1.73 (m, 2H), 1.68-1.58 (m, 2H).

C. N$^1$-(2-Cyclopentyloxy-phenyl)-ethane-1,2-diamine. $^1$H NMR (400 MHz, CDCl$_3$): 6.82 (dt, J=7.6, 1.3 Hz, 1H), 6.76-6.74 (m, 1H), 6.66-6.61 (m, 2H), 4.78-4.74 (m, 1H), 3.38 (br s, 2H), 3.29 (t, J=5.7 Hz, 2H), 3.06-2.91 (m, 2H), 1.96-1.87 (m, 4H), 1.86-1.75 (m, 2H), 1.69-1.55 (m, 2H).

D. (3-{[2-(2-Cyclopentyloxy-phenylamino)-ethylamino]-methyl}-phenyl)piperidin-1-yl-methanone. MS (ESI): mass calculated for C$_{26}$H$_{35}$N$_3$O$_2$, 421.27, m/z found, 422.3 [M+H]$^+$. $^1$H NMR (400 MHz, CDCl$_3$): 7.41-7.39 (m, 1H), 7.35-7.32 (m, 2H), 7.26-7.24 (m, 1H), 6.83 (dt, J=7.6, 1.4 Hz, 1H), 6.76 (dd, J=7.6, 1.2 Hz, 1H), 6.65-6.61 (m, 2H), 4.80-4.75 (m, 1H), 3.85 (s, 2H), 3.70 (br s, 2H), 3.32 (br s, 2H), 3.27 (t, J=5.8 Hz, 2H), 2.92 (t, J=5.8 Hz, 2H), 1.96-1.73 (m, 7H), 1.67-1.57 (m, 6H), 1.50 (br s, 2H).

Example 8

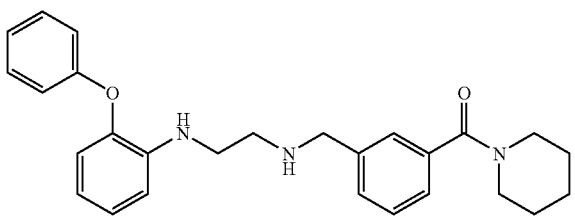

(3-{[2-(2-Phenoxy-phenylamino)-ethylamino]-methyl}-phenyl)-piperidin-1-yl-methanone The title compound was prepared as in Example 1, steps C-E substituting 2-phenoxy-phenylamine for 2-isopropoxy-phenylamine in step C.

A. N$^1$-(2-Phenoxy-phenyl)-ethane-1,2-diamine. MS (ESI): mass calculated for C$_{14}$H$_{16}$N$_2$O, 228.13; m/z found, 229.2 [M+H]$^+$. $^1$H NMR (400 MHz, CDCl$_3$): 8.19 (br s, 1H), 7.28-6.67 (m, 9H), 3.55-3.15 (m, 4H). $^{13}$C NMR (100 MHz, CDCl$_3$): 144.2, 137.7, 129.6, 124.5, 123.1, 118.7, 118.6, 118.0, 112.7, 41.5, 39.0.

B. (3-{[2-(2-Phenoxy-phenylamino)-ethylamino]-methyl}-phenyl)-piperidin-1-yl-methanone. MS (ESI): mass calculated for C$_{27}$H$_{31}$N$_3$O$_2$, 429.24; m/z found, 430.4 [M+H]$^+$. $^1$H NMR (400 MHz, CDCl$_3$): 7.36-7.22 (m, 6H), 7.05-6.95 (m, 4H), 6.84 (dd, J=7.8, 1.4 Hz, 1H), 6.75 (dd, J=8.0, 1.4 Hz, 1H), 6.64 (dt, J=7.8, 1.4 Hz, 1H), 4.54 (br s, 1H), 3.76 (s, 2H), 3.69 (br s, 2H), 3.39-3.25 (m, containing a t, J=5.8 Hz, 4H), 2.85 (t, J=6.0 Hz, 2H), 1.85 (br s, 1H), 1.65 (br s, 4H), 1.48 (br s, 2H). $^{13}$C NMR (100 MHz, CDCl$_3$): 170.2, 157.5, 143.1, 141.7, 140.5, 140.5, 136.6, 136.5, 129.6, 128.9, 128.4, 127.7, 126.3, 125.6, 125.3, 124.9, 122.6, 119.3, 117.3, 116.7, 111.6, 64.5, 53.1, 48.7, 47.9, 43.1, 26.4, 25.5, 24.5.

Example 9

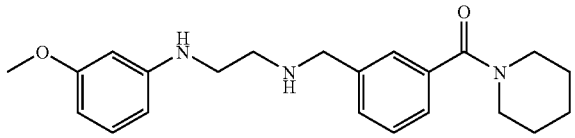

(3-{[2-(3-Methoxy-phenylamino)-ethylamino]-methyl}-phenyl)-piperidin-1-yl-methanone The title compound was prepared as in Example 1, steps C-E, substituting 3-methoxy-phenylamine for 2-isopropoxy-phenylamine in step C.

A. N$^1$-(3-Methoxy-phenyl)-ethane-1,2-diamine. MS (ESI): mass calculated for C$_9$H$_{14}$N$_2$O, 166.11; m/z found, 167.1 [M+H]$^+$. $^1$H NMR (400 MHz, DMSO-d$_6$, HCl salt): 8.18 (br s, 2H), 7.00-6.96 (m, 1H), 6.22-6.15 (m, 3H), 5.93 (br s, 1H), 3.67 (s, 3H), 3.35-3.26 (m, 2H), 5.93 (br s, 2H). $^{13}$C NMR (100 MHz, DMSO-d$_6$): 160.4, 149.4, 129.7, 105.4, 101.9, 98.0, 54.7, 25.5.

B. (3-{[2-(3-Methoxy-phenylamino)-ethylamino]-methyl}-phenyl)-piperidin-1-yl-methanone. MS (ESI): mass calculated for C$_{22}$H$_{29}$N$_3$O$_2$, 367.23, m/z found, 368.3 [M+H]$^+$, 390.3 [M+Na]$^+$. $^1$H NMR (400 MHz, CDCl$_3$): 7.37-7.23 (m, 4H), 7.06 (t, J=8.1 Hz, 1H), 6.25 (dt, J=8.0, 2.2 Hz, 2H), 6.18 (t, J=2.2 Hz, 1H), 2.10 (s, 2H), 3.75 (s, 3H), 3.69 (br s, 2H), 3.31 (br s, 2H), 3.21 (t, J=5.6 Hz, 2H), 2.89 (t, J=5.9 Hz, 2H), 1.66 (br s, 4H), 1.49 (br s, 2H). $^{13}$C NMR (100 MHz, CDCl$_3$): 170.1, 160.7, 149.7, 140.1, 136.6, 129.9, 129.0, 128.4, 126.4, 125.4, 106.0, 102.5, 98.8, 55.0, 53.1, 48.7, 47.8, 43.1, 26.4, 25.5, 24.5.

Example 10

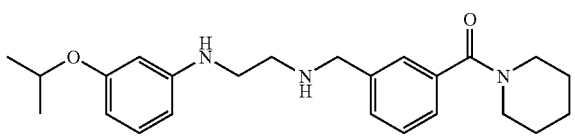

(3-{[2-(3-Isopropoxy-phenylamino)-ethylamino]-methyl}-phenyl)-piperidin-1-yl-methanone The title compound was prepared as in Example 1, steps C-E, substituting 3-isopropoxyphenylamine for 2-isopropoxyphenylamine in step C.

A. $N^1$-(3-Isopropoxy-phenyl)-ethane-1,2-diamine. MS (ESI): mass calculated for $C_{11}H_{18}N_2O$, 194.14; m/z found, 195.2 [M+H]$^+$. $^1$H NMR (400 MHz, CDCl$_3$): 7.04 (t, J=8.1 Hz, 1H), 6.27-6.19 (m, 2H), 6.19 (br s, 1H), 4.51 (hept, J=6.1 Hz, 1H), 3.41-3.22 (m, 6H), 2.93 (br s, 2H), 1.31 (d, J=6.1 Hz, 6H). $^{13}$C NMR (100 MHz, CDCl$_3$): 158.9, 149.3, 129.8, 105.8, 104.4, 100.8, 69.5, 44.8, 40.1, 21.9.

B. (3-{[2-(3-Isopropoxy-phenylamino)-ethylamino]-methyl}-phenyl)-piperidin-1-yl-methanone. MS (ESI): mass calculated for $C_{24}H_{33}N_3O_2$, 395.26; m/z found, 396.4 [M+H]$^+$, 418.4 [M+Na]$^+$. $^1$H NMR (400 MHz, CDCl$_3$): 7.34-7.23 (m, 4H), 7.03 (t, J=8.0 Hz, 1H), 4.49 (hept, J=6.1 Hz, 1H), 3.80 (s, 2H), 3.69 (br s, 2H), 3.30 (br s, 2H), 3.18 (t, J=5.5 Hz, 2H), 2.85 (t, J=5.5 Hz, 2H), 1.65-1.45 (m, 6H), 1.30 (d, J=6.0 Hz, 6H). $^{13}$C NMR (100 MHz, CDCl$_3$): 170.1, 158.9, 149.7, 140.4, 136.4, 129.7, 128.9, 128.3, 126.2, 125.1, 105.8, 104.2, 100.6, 69.3, 53.1, 48.6, 47.8, 43.2, 42.9, 26.4, 25.4, 24.4, 22.0.

Example 11

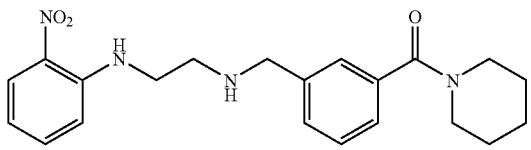

(3-{[2-(2-Nitro-phenylamino)-ethylamino]-methyl}-phenyl)-piperidin-1-yl-methanone A. $N^1$-(2-Nitro-phenyl)-ethane-1,2-diamine. To a mixture of ethylenediamine (1.05 g, 17.5 mmol) and K$_2$CO$_3$ (2.44 g, 17.7 mmol) in anhydrous CH$_3$CN (300 mL) heated to 70° C., a solution of o-fluoronitrobenzene (1.25 g, 8.87 mmol) in CH$_3$CN (50 mL) was added dropwise over 2 h. The resulting suspension was stirred at 70° C. for 1 h, and then allowed to cool to 25° C. and stirred for 18 h. The suspension was filtered, and the filtrate was concentrated under reduced pressure. The crude residue was partitioned between H$_2$O (200 mL) and CH$_2$Cl$_2$ (200 mL), and the organic layer was washed with H$_2$O (2×200 mL), dried (Na$_2$SO$_4$), filtered, and concentrated under reduced pressure to provide a bright yellow semisolid (1.5 g, 78%). MS (ESI): mass calculated for $C_8H_{11}N_3O_2$, 181.09; m/z found, 182.1 [M+H]$^+$. $^1$H NMR (400 MHz, CDCl$_3$): 8.26 (br s, 1H), 8.17 (dd, J=8.6, 1.6 Hz, 1H), 7.46-7.41 (m, 1H), 6.86 (dd, J=8.7, 0.82 Hz, 1H), 6.63-6.62 (m, 1H), 3.39 (q, J=5.7 Hz, 2H), 3.06 (t, J=5.7 Hz, 2H). $^{13}$C NMR (100 MHz, CDCl$_3$): 40.8, 45.7, 113.4, 115.3, 127.1, 136.2, 145.6.

B. (3-{[2-(2-Nitro-phenylamino)-ethylamino]-methyl}-phenyl)-piperidin methanone. The title compound was prepared as in Example 1, steps D and E, substituting $N^1$-(2-nitro-phenyl)-ethane-1,2-diamine for $N^1$-(2-isoproxy-phenyl)ethane-1,2-diamine in step E, yielding a bright yellow semisolid (2.18 g, 89%). MS (ESI): mass calculated for $C_{21}H_{26}N_4O_3$, 382.20; m/z found, 383.2 [M+H]$^+$, 405.2 [M+Na]$^+$. $^1$H NMR (400 MHz, CDCl$_3$): 8.38 (br s, 1H), 8.15 (dd, J=8.6, 1.6 Hz, 1H), 7.44-7.33 (m, 4H), 7.29-7.25 (m, 1H), 6.83 (dd, J=8.6, 0.7 Hz, 1H), 6.64-6.60 (m, 1H), 3.87 (s, 2H), 3.70 (br s, 2H), 3.38 (q, J=5.8 Hz, 2H), 3.33 (br s, 2H), 3.06 (t, J=5.8 Hz, 2H), 1.67 (br s, 4H), 1.50 (br s, 2H). $^{13}$C NMR (100 MHz, CDCl$_3$): 170.2, 145.4, 140.5, 136.7, 136.2, 131.9, 129.0, 128.5, 126.8, 126.4, 125.4, 115.2, 113.9, 53.5, 48.8, 47.3, 43.1, 42.6, 26.5, 25.6, 24.6.

Example 12

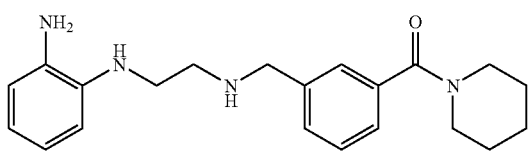

(3-{[2-(2-Amino-phenylamino)-ethylamino]-methyl}-phenyl)-piperidin-1-yl-methanone To a solution of (3-{[2-(2-nitro-phenylamino)-ethylamino]-methyl}-phenyl)piperidin-1-yl-methanone (Example 11; 0.060 g, 0.16 mmol) in EtOH (1.6 mL) was added cyclohexadiene (0.55 mL) followed by Pd/C (10 wt %, 0.02 g), and the resulting suspension was heated to 100° C. for 45 min. The suspension was filtered (diatomaceous earth), and the filtrate was concentrated under reduced pressure. The crude residue was purified by column chromatography (0-5% CH$_3$OH/CH$_2$Cl$_2$) to provide the desired product as a colorless oil (0.034 g, 61%). MS (ESI): mass calculated for $C_{21}H_{28}N_4O$, 352.23; m/z found, 353.2 [M+H]$^+$, 375.2 [M+Na]$^+$. $^1$H NMR (400 MHz, CDCl$_3$): 7.38-7.32 (m, 3H), 7.26-7.24 (m, 1H), 6.80 (dt, J=5.4, 1.9 Hz, 1H), 6.72-6.64 (m, 3H), 3.84 (br s, 2H), 3.70 (br s, 2H), 3.32 (br s, 2H), 3.21 (t, J=5.7 Hz, 2H), 2.94 (t, J=5.7 Hz, 2H), 1.67 (br s, 4H), 1.50 (br s, 1H). $^{13}$C NMR (100 MHz, CDCl$_3$): 170.3, 140.7, 137.7, 136.7, 134.6, 129.1, 128.4, 126.5, 125.3, 120.5, 118.7, 116.3, 112.0, 53.3, 48.1, 43.8, 29.7, 26.5, 24.6.

Example 13

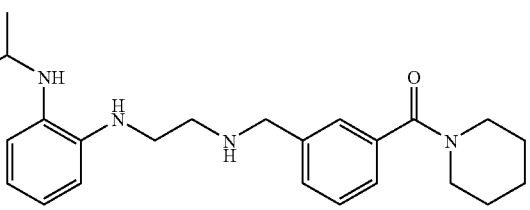

(3-{[2-(2-Isopropylamino-phenylamino)-ethylamino]-methyl}-phenyl)-piperidin-1-yl-methanone A. [2-(2-Nitro-phenylamino)-ethyl]-[3-(piperidine-1-carbonyl)-benzyl]-carbamic acid tert-butyl ester. To a solution of (3-{[2-(2-nitro-phenylamino)-ethylamino]-methyl}-phenyl)-piperidin-1-yl-methanone (Example 11; 2.18 g, 5.70 mmol) in CH$_2$Cl$_2$ (25 mL) was added a solution of di-tert-butyl-dicarbonate (1.24 g, 5.68 mmol) in CH$_2$Cl$_2$ (32 mL), and the resulting solution was stirred at 25° C. for 2 h. The solvent was removed in vacuo, and the residue was partitioned between H$_2$O (100 mL) and EtOAc (100 mL). The organic layer was dried (Na$_2$SO$_4$), filtered, and concentrated under reduced pressure. The crude residue was purified by column chromatography (0-8% CH$_3$OH/CH$_2$Cl$_2$) to provide a bright yellow semisolid (2.36 g, 86%). MS (ESI): mass calculated for C$_{26}$H$_{34}$N$_4$O$_5$, 482.25; m/z found, 483.2 [M+H]$^+$, 505.2 [M+Na]$^+$. $^1$H NMR (400 MHz, CDCl$_3$): 8.24 (br s, 1H), 8.09 (d, J=8.5 Hz, 1H), 7.44-7.27 (m, 5H), 6.88-6.83 (m, 1H), 6.61 (t, J=7.6 Hz, 1H), 4.50-4.54 (m, 2H), 3.68-3.30 (m, 8H), 1.65 (br s, 4H), 1.48 (br s, 11H). $^{13}$C NMR (100 MHz, CDCl$_3$): 170.1, 156.0, 145.6, 139.0, 137.2, 136.5, 132.2, 129.0, 128.3, 126.9, 126.4, 126.0, 115.7, 114.0, 80.8, 51.6, 50.3, 49.0, 46.1, 45.6, 43.3, 41.5, 28.6, 26.7, 25.9, 24.8.

B. [2-(2-Amino-phenylamino)-ethyl]-[3-(piperidine-1-carbonyl)-benzyl]-carbamic acid tert-butyl ester. The title intermediate was prepared as in Example 12, substituting [2-(2-nitro-phenylamino)-ethyl]-[3-(piperidine-1-carbonyl)-benzyl]-carbamic acid tert-butyl ester for (3-{[2-(2-nitro-phenylamino)-ethylamino]-methyl}-phenyl)-piperidin-1-yl-methanone, yielding a tan semisolid (1.4 g, 62%). MS (ESI): mass calculated for C$_{26}$H$_{36}$N$_4$O$_3$, 452.28; m/z found, 453.3 [M+H]$^+$, 475.2 [M+Na]$^+$. $^1$H NMR (400 MHz, CDCl$_3$): 8.24 (br s, 1H), 8.09 (d, J=8.5 Hz, 1H), 7.44-7.27 (m, 5H), 6.88-6.83 (m, 1H), 6.61 (t, J=7.6 Hz, 1H), 4.54-4.50 (m, 2H), 3.68-3.30 (m, 8H), 1.65 (br s, 4H), 1.48 (br s, 11H). $^{13}$C NMR (100 MHz, CDCl$_3$): 170.1, 156.0, 145.6, 139.0, 137.2, 136.5, 132.2, 129.0, 128.3, 126.9, 126.4, 126.0, 115.7, 114.0, 80.8, 51.6, 50.3, 49.0, 46.1, 45.6, 43.3, 41.5, 28.6, 26.7, 25.9, 24.8.

C. [2-(2-Isopropylamino-phenylamino)-ethyl]-[3-(piperidine-1-carbonyl)-benzyl]-carbamic acid tert-butyl ester. To a solution of [2-(2-amino-phenylamino)ethyl]-[3-(piperidine-1-carbonyl)-benzyl]-carbamic acid tert-butyl ester (0.060 g, 0.133 mmol) in DMF (1.3 mL) was added K$_2$CO$_3$ (0.092 g, 0.67 mmol). 2-Iodopropane (0.112 g, 0.66 mmol) was added to the resulting suspension, and the mixture was stirred at 50° C. for 6 h. The reaction mixture was partitioned with CH$_2$Cl$_2$ (30 mL) and 1 N NaOH (30 mL), and the organic layer was dried (Na$_2$SO$_4$), filtered, and concentrated under reduced pressure. The crude residue was purified by column chromatography (0-5% CH$_3$OH/CH$_2$Cl$_2$) to provide a colorless oil (0.032 g, 49%). MS (ESI): mass calculated for C$_{29}$H$_{42}$N$_4$O$_3$, 494.33; m/z found, 495.3 [M+H]$^+$, 517.3 [M+Na]$^+$. $^1$H NMR (400 MHz, CDCl$_3$): 7.36-7.32 (m, 1H), 7.28-7.24 (m, 4H), 6.77-6.53 (m, 4H), 4.51-4.46 (m, 2H), 3.69 (br s, 2H), 3.58 (br s, 2H), 3.42 (br s, 1H), 3.28 (br s, 2H), 3.23 (t, J=6.0 Hz, 2H), 1.66 (br s, 4H), 1.51-1.44 (m, 11H), 1.22 (d, J=6.3 Hz, 6H).

D. (3-{[2-(2-Isopropylamino-phenylamino)-ethylamino]-methyl}-phenyl)piperidin-1-yl-methanone. To a solution of [2-(2-isopropylamino-phenylamino)ethyl]-[3-(piperidine-1-carbonyl)-benzyl]-carbamic acid tert-butyl ester (0.026 g, 0.053 mmol) in CH$_2$Cl$_2$ (0.53 mL) was added 1 M HCl in dioxane (0.10 mL), and the mixture was stirred at 25° C. for 1 h. The reaction mixture was partitioned with 1 M NaOH (20 mL) and CH$_2$Cl$_2$ (20 mL), and the organic layer was dried (MgSO$_4$), filtered, and concentrated under reduced pressure to give the desired product as a white solid (0.020 g, 96%). MS (ESI): mass calculated for C$_{24}$H$_{34}$NO, 394.27; m/z found, 395.2 [M+H]$^+$, 417.3 [M+Na]$^+$. $^1$H NMR (400 MHz, CDCl$_3$): 7.40-7.32 (m, 3H), 7.27-7.24 (m, 1H), 6.80-6.73 (m, 2H), 6.69-6.66 (m, 2H), 3.85 (s, 2H), 3.70 (br s, 2H), 3.58 (hept, J=6.3 Hz, 1H), 3.32 (br s, 2H), 3.21 (t, J=5.8 Hz, 2H), 2.94 (t, J=5.8 Hz, 2H), 1.67 (br s, 4H), 1.50 (br s, 2H), 1.23 (d, J=6.3 Hz, 6H).

Example 14

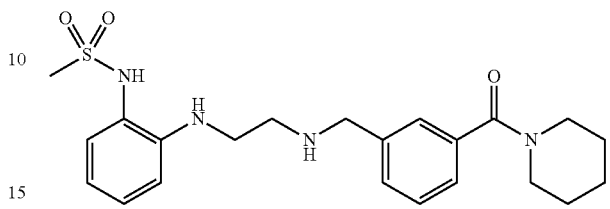

N-(2-{2-[3-(Piperidine-1-carbonyl)-benzylamino]-ethylamino}-phenyl)methanesulfonamide A. [2-(2-Methanesulfonylamino-phenylamino)-ethyl]-[3-(piperidine-1-carbonyl)-benzyl]-carbamic acid tert-butyl ester. To a solution of [2-(2-amino-phenylamino)-ethyl]-[3-(piperidine-1-carbonyl)-benzyl]-carbamic acid tert-butyl ester (Example 13, step B; 0.10 g, 0.22 mmol) in CH$_2$Cl$_2$ (4 mL) was added Et$_3$N (0.033 g, 0.33 mmol) and methanesulfonyl chloride (0.028 g, 0.24 mmol), and the resulting mixture was stirred at 25° C. for 17 h. The reaction mixture was treated with satd NH$_4$Cl (10 mL), H$_2$O (10 mL) and CH$_2$Cl$_2$ (20 mL), and the aqueous layer was extracted with CH$_2$Cl$_2$ (3×20 mL). The combined organic layers were washed with brine, dried (MgSO$_4$), filtered, and concentrated under reduced pressure. The crude residue was purified by preparative TLC (30% acetone/hexanes) to provide the desired product (0.060 g, 51%). MS (ESI): mass calculated for C$_{27}$H$_{38}$N$_4$O$_5$S, 530.26; m/z found, 531.2 [M+H]$^+$.

B. N-(2-{2-[3-(Piperidine-1-carbonyl)-benzylamino]-ethylamino}-phenyl)methanesulfonamide. The title compound was prepared as in Example 13, step D, substituting [2-(2-methanesulfonyl-amino-phenylamino)-ethyl]-[3-(piperidine-1-carbonyl)-benzyl]-carbamic acid tert-butyl ester for 2-(2-isopropylamino-phenylamino)-ethyl]-[3-(piperidine-1-carbonyl)-benzyl]-carbamic acid tert-butyl ester, yielding the desired sulfonamide (0.020 g, 42%). $^1$H NMR (400 MHz, CDCl$_3$): 7.47 (br s, 1H), 7.33-7.28 (m, 2H), 7.20-7.13 (m, 3H), 6.68-6.64 (m, 2H), 3.84 (s, 2H), 3.74-3.71 (m, 2H), 3.31 (br s, 2H), 3.23 (t, J=5.5 Hz, 2H), 3.02 (s, 3H), 2.88 (t, J=5.5 Hz, 2H), 1.67-1.50 (m, 6H).

Example 15

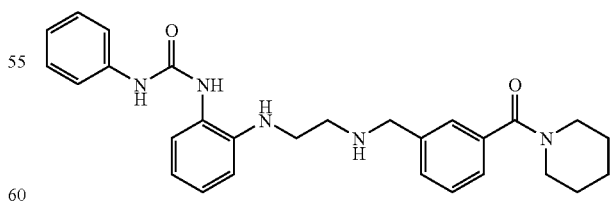

1-Phenyl-3-(2-{2-[3-(piperidine-1-carbonyl)-benzylamino]-ethylamino}-phenyl)-urea A. N-Benzyl-N'-(2-nitro-phenyl)-ethane-1,2-diamine. The title intermediate was prepared as in Example 11, step A, substituting N¹-benzyl-ethane-1,2-diamine for ethylenediamine. MS (ESI): mass calculated for $C_{15}H_{17}N_3O_2$, 271.13; m/z found, 272.1 [M+H]⁺. ¹H NMR (400 MHz, $CDCl_3$): 8.40 (br s, 1H), 8.20 (dd, J=8.6, 1.5 Hz, 1H), 7.48-7.25 (m, 6H), 6.85 (d, J=8.5 Hz, 1H), 6.65 (t, J=8.3 Hz, 1H), 3.88 (s, 2H), 3.43 (dd, J=11.4, 5.5 Hz, 2H), 3.02 (t, J=6.0 Hz, 2H).

B. 1-[2-(2-Benzylamino-ethylamino)-phenyl]-3-phenyl-urea. Substitution of N-benzyl-N'-(2-nitro-phenyl)-ethane-1,2-diamine for (3-{[2-(2-nitro-phenylamino) -ethylamino]-methyl}-phenyl)-piperidin-1-yl-methanone in Example 13, step A, gave benzyl-[2-(2-nitro-phenylamino)-ethyl]-carbamic acid tert-butyl ester, the nitro group of which was reduced as in Example 7, step B, to provide [2-(2-amino-phenylamino)-ethyl]-benzyl-carbamic acid tert-butyl ester. Substitution of the ester and phenylisocyanate for [2-(2-amino-phenylamino)-ethyl]-[3-(piperidine-1-carbonyl)-benzyl]-carbamic acid tert-butyl ester and methanesulfonylchloride in the procedure of Example 14, step A, gave benzyl-{2-[2-(3-phenyl-ureido)-phenylamino]-ethyl}-carbamic acid tert-butyl ester, which was converted to the title intermediate by deprotection as in Example 13, step D. MS (ESI): mass calculated for $C_{22}H_{24}N_4O$, 360.20; m/z found, 361.2 [M+H]⁺. ¹H NMR (400 MHz, $CDCl_3$): 7.24-7.05 (m, 1H), 6.94-6.90 (m, J=7.3 Hz, 1H), 6.66-6.62 (m, 3H), 6.29 (br s, 1H), 4.53 (br s, 1H), 3.65 (s, 2H), 3.12 (t, J=5.7 Hz, 2H), 2.80-2.75 (m, 2H).

C. 1-[2-(2-Amino-ethylamino)-phenyl]-3-phenyl-urea. The title intermediate was prepared as in Example 7, step B, substituting 1-[2-(2-benzylamino -ethylamino)-phenyl]-3-phenyl-urea for 1-cyclopentyloxy-2-nitro-benzene. MS (ESI): mass calculated for $C_{15}H_{18}N_4O$, 370.15; m/z found, 371.1 [M+H]⁺. ¹H NMR (400 MHz, $CDCl_3$): 7.35-7.13 (m, 6H), 7.03-6.99 (m, 1H), 6.78-6.69 (m, 2H), 3.20-3.10 (m, 2H), 2.90-2.85 (m, 2H), 2.00-2.40 (br m, 3H).

D. 1-Phenyl-3-(2-{2-[3-(piperidine-1-carbonyl)-benzylamino]-ethylamino}-phenyl)-urea. The title compound was prepared as in Example 1, steps D and E, substituting 1-[2-(2-amino-ethylamino)-phenyl]-3-phenyl-urea for N¹-(2-isoproxy-phenyl)-ethane-1,2-diamine in step E. MS (ESI): mass calculated for $C_{28}H_{33}N_5O_2$, 471.26; m/z found, 472.2 [M+H]⁺. ¹H NMR (400 MHz, $CDCl_3$): 8.17 (br s, 1H), 7.48-7.11 (m, 9H), 7.05-6.95 (m, 1H), 6.92-6.85 (m, 1H), 6.64 (dt, J=7.6, 1.0 Hz, 1H), 6.53 (d, J=7.2 Hz, 1H), 3.73 (s, 2H), 3.65 (br s, 2H), 3.28 (br s, 2H), 3.08 (dd, J=5.6, 5.0 Hz, 2H), 2.80 (dd, J=5.5, 5.1 Hz, 2H), 2.60-2.40 (br m, 2H), 1.60 (br s, 4H), 1.44 (br s, 2H).

Example 16

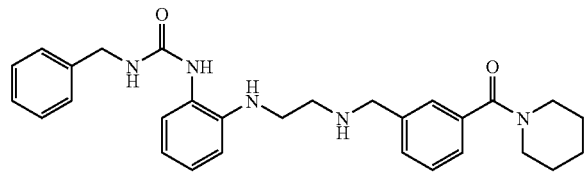

1-Benzyl-3-(2-{2-[3-(piperidine-1-carbonyl)-benzylamino]-ethylamino}-phenyl)-urea A. 1-[2-(2-Amino-ethylamino)-phenyl]-3-benzyl-urea. Substitution of N-(2-benzylamino-ethyl)-benzene-1,2-diamine and benzylisocyanate for [2-(2-aminophenylamino)-ethyl]-[3-(piperidine-1-carbonyl)-benzyl]-carbamic acid tert-butyl ester and methanesulfonylchloride in Example 14, step A, provided benzyl-{2-[2-(3-benzyl-ureido)-phenylamino]-ethyl}-carbamic acid tert-butyl ester, deprotection of which, as in Example 13, step D, gave 1-benzyl-3-[2-(2-benzylamino-ethylamino)-phenyl]-urea. The benzylamine intermediate was then converted to the title intermediate by its substitution for 1-cyclopentyloxy-2-nitro-benzene in the procedure of Example 7, step B. ¹H NMR (400 MHz, $CD_3OD$): 7.35-7.30 (m, 3H), 7.28-7.08 (m, 4H), 6.80-6.76 (m, 1H), 6.74-6.68 (m, 1H), 4.38 (s, 2H), 3.49 (t, J=5.6 Hz, 2H), 3.11 (t, J=5.9 Hz, 2H).

B. 1-Benzyl-3-(2-{2-[3-(piperidine-1-carbonyl)-benzylamino]-ethylamino}-phenyl)-urea. The title compound was prepared as in Example 1, steps D and E substituting 1-[2-(2-amino-ethylamino)-phenyl]-3-benzyl-urea for N¹-(2-isoproxy-phenyl)-ethane-1,2-diamine in step E. MS (ESI): mass calculated for $C_{29}H_{35}N_5O_2$, 485.28, m/z found, 486.3 [M+H]⁺. ¹H NMR (400 MHz, $CD_3OD$): 7.43-7.11 (m, 11H), 6.75 (d, J=7.6 Hz, 1H), 6.67 (dt, J=7.6, 1.1 Hz, 1H), 4.32 (s, 2H), 3.84 (s, 2H), 3.64 (br s, 2H), 4.06 (t, J=5.8 Hz, 2H), 3.02 (t, J=5.8 Hz, 2H), 1.75-1.45 (m, 4H), 1.47 (br s, 2H).

Example 17

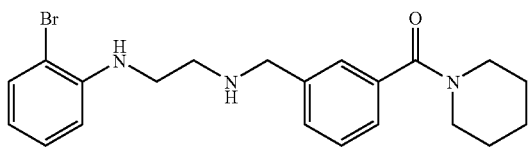

(3-{[2-(2-Bromo-phenylamino)-ethylamino]-methyl}-phenyl)-piperidin-1-yl-methanone The title compound was prepared as in Example 1, steps C-E, substituting 2-bromo-phenylamine for 2-isopropoxyphenylamine in step C.

A. N¹-(2-Bromo-phenyl)-ethane-1,2-diamine. MS (ESI): mass calculated for $C_8H_{11}BrN_2$, 214.01; m/z found, 215.0 [M+H]⁺. ¹H NMR (400 MHz, $CDCl_3$): 7.42 (dd, J=7.8, 1.5 Hz, 1H), 7.18 (dt, J=7.4, 1.5 Hz, 1H), 6.67 (dd, J=8.1, 1.3 Hz, 1H), 6.58 (dt, J=8.0, 1.4 Hz, 1H), 3.28 (t, J=5.7 Hz, 2H), 3.04 (br s, 3H), 2.95 (t, J=5.9 Hz, 2H). ¹³C NMR (100 MHz, $CDCl_3$): 144.5, 132.5, 128.7, 117.7, 111.4, 108.8, 41.2, 37.4.

B. (3-{[2-(2-Bromo-phenylamino)-ethylamino]-methyl}-phenyl)-piperidin methanone. MS (ESI): mass calculated for $C_{21}H_{26}BrN_3O$, 415.13; m/z found, 416.1 [M+H]⁺. ¹H NMR (400 MHz, $CDCl_3$): 7.41-7.38 (m, 4H), 7.35-7.32 (m, 1H), 7.27-7.24 (m, 1H), 6.63-6.61 (m 1H), 6.55 (t, J=7.5 Hz, 1H), 4.85 (br s, 1H), 3.84 (br s, 2H), 3.69 (br s, 2H), 3.31-3.23 (m, 4H), 2.94-2.92 (m, 2H), 1.83-1.48 (m, 7H). ¹³C NMR (100 MHz, $CDCl_3$): 170.2, 145.1, 140.5, 136.6, 132.3, 128.9, 128.4, 126.3, 125.3, 117.6, 111.3, 109.8, 53.0, 48.7, 47.5, 43.1, 26.4, 25.5, 24.5.

Example 18

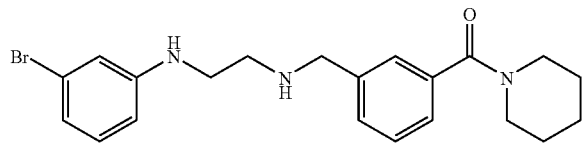

(3-{[2-(3-Bromo-phenylamino)-ethylamino]-methyl}-phenyl)-piperidin-1-yl-methanone To a solution of 3-bromoaniline (0.50 g, 2.9 mmol) in diethyl ether (Et$_2$O, 5 mL) was added 4 M HCl in dioxane (1 mL), and the mixture was stirred at 25° C. for 1 h. Solvent was removed under reduced pressure, and the resulting HCl salt was dissolved in 2-(2-methoxyethoxy)ethanol (2 mL). 2-Oxazolidinone (0.429 g, 4.93 mmol) was added, and the reaction mixture was heated to 180° C. for 24 h. The collected crude solid was purified by column chromatography (0-10% (1% NH$_4$OH in MeOH)/CH$_2$Cl$_2$) to provide N$^1$-(3-bromo-phenyl)-ethane-1,2-diamine (0.10 g, 16%). 3-(Piperidine-1-carbonyl)-benzaldehyde (Example 1, step D; 0.091 g, 0.42 mmol) was added to a solution of the phenyl-diamine in 1,2-dichloroethane (10 mL), and the reaction mixture was stirred at 25° C. for 15 min. The mixture was treated with NaBH(OAc)$_3$ (0.128 g, 0.604 mmol), and the resulting suspension was stirred at 25° C. for 18 h. The suspension was partitioned with satd NH$_4$Cl (20 mL) and CH$_2$Cl$_2$ (20 mL), and the aqueous layer was extracted with CH$_2$Cl$_2$ (3×20 mL). The combined organic layers were washed with brine (50 mL), dried (MgSO$_4$), filtered, and concentrated under reduced pressure. The crude residue was purified by column chromatography (2-10% CH$_3$OH/CH$_2$Cl$_2$), and then by preparative TLC (10% CH$_3$OH/CH$_2$Cl$_2$) to provide the desired product (0.060 g, 34%). MS (ESI): mass calculated for C$_{21}$H$_{26}$BrN$_3$O, 415.13; m/z found, 416.1 [M+H]$^+$. $^1$H NMR (400 MHz, CDCl$_3$): 7.28-7.26 (m, 3H), 7.21-7.16 (m, 1H), 6.93 (t, J=8.0 Hz, 1H), 6.74-6.71 (m, 1H), 6.67 (t, J=2.0 Hz, 1H), 6.47-6.44 (m, 1H), 4.23 (br s, 1H), 3.75 (s, 2H), 3.64 (br s, 2H), 3.25 (br s, 2H), 3.10 (t, J=5.6 Hz, 2H), 2.83-2.80 (m, 2H), 1.60-1.43 (m, 6H).

Example 19

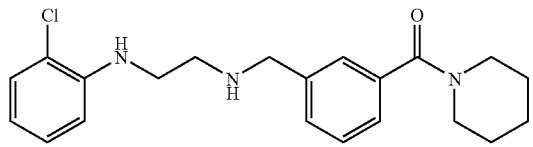

(3-{[2-(2-Chloro-phenylamino)-ethylamino]-methyl}-phenyl)-piperidin-1-yl-methanone The title compound was prepared as in Example 18, substituting 2-chloroaniline for 3-bromoaniline. MS (ESI): mass calculated for C$_{26}$H$_{23}$ClN$_3$O, 371.18; m/z found, 372.2 [M+H]$^+$. $^1$H NMR (400 MHz, CHCl$_3$): 7.40-7.10 (m, 6H), 6.91 (dd, J=8.0, 1.3 Hz, 1H), 6.84 (dt, J=7.8, 1.3 Hz, 1H), 6.66-6.59 (m, 2H), 4.82 (br s, 1H), 3.85 (s, 2H), 3.66 (br s, 2H), 3.40-3.25 (m, 4H), 2.93 (t, J=5.6 Hz, 2H), 1.74-1.49 (m, 8H).

Example 20

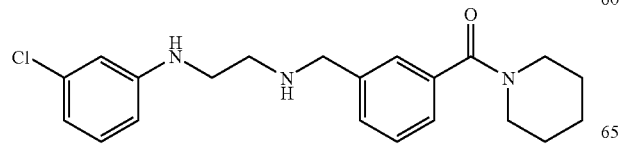

(3-{[2-(3-Chloro-phenylamino)-ethylamino]-methyl}-phenyl)-piperidin-1-yl-methanone The title compound was prepared as in Example 18, substituting 3-chloroaniline for 3-bromoaniline. MS (ESI): mass calculated for C$_{21}$H$_{26}$ClN$_3$O, 371.9; m/z found, 372.2 [M+H]$^+$. $^1$H NMR (400 MHz, CDCl$_3$): 7.29 (br s, 3H), 7.19 (br s, 1H), 6.98 (br t, J=7.9 Hz, 1H), 6.57 (d, J=7.6 Hz, 1H), 6.51 (br s, 1H), 6.41 (d, J=7.7 Hz, 1H), 3.76 (br s, 2H), 3.63 (br s, 2H), 3.24 (br s, 2H), 3.11 (br s, 2H), 1.60-1.43 (m, 6H).

Example 21

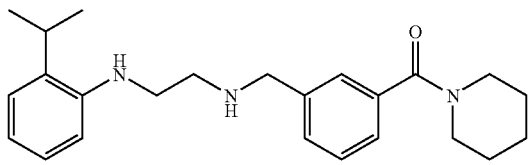

(3-{[2-(2-Isopropyl-phenylamino)-ethylamino]-methyl}-phenyl)-piperidin-1-yl-methanone The title compound was prepared as in Example 1, steps C-E substituting 2-isopropyl-phenylamine for 2-isopropoxy-phenylamine in step C.

A. N$^1$-(2-Isopropyl-phenyl)-ethane-1,2-diamine. MS (ESI): mass calculated for C$_{11}$H$_{18}$N$_2$, 178.15; m/z found, 179.2 [M+H]$^+$. $^1$H NMR (400 MHz, CDCl$_3$): 7.14 (dd, J=7.6, 1.4 Hz, 1H), 7.09 (dt, J=7.7, 1.4 Hz, 1H), 6.73 (dt, J=7.5, 1.0 Hz, 1H), 6.64 (d, J=8.0 Hz, 1H), 3.25 (t, J=5.5 Hz, 2H), 2.99 (t, J=6.0 Hz, 2H), 2.94 (hept, J=6.7 Hz, 1H), 1.24 (d, J=6.7 Hz, 6H). $^{13}$C NMR (100 MHz, CDCl$_3$): 144.7, 132.6, 126.6, 125.0, 117.5, 110.5, 45.8, 40.7, 27.0, 22.3.

B. (3-{[2-(2-Isopropyl-phenylamino)-ethylamino]-methyl}-phenyl)-piperidin-1-yl-methanone. MS (ESI): mass calculated for C$_{24}$H$_{33}$N$_3$O, 379.26; m/z found, 380.3 [M+H]$^+$, 402 [M+Na]$^+$. $^1$H NMR (400 MHz, CDCl$_3$): 7.38-7.31 (m, 3H), 7.26-7.24 (m, 1H), 7.15-7.08 (m, 2H), 6.73 (dt, J=7.5, 1.0 Hz, 1H), 6.63 (dd, J=7.8, 1.0 Hz, 1H), 3.84 (s, 2H), 3.69 (br s, 2H), 3.30-3.23 (m, containing a t at 3.25, J=5.4 Hz, 4H), 2.97-2.89 (m, 3H), 1.66 (br s, 4H), 1.48 (br s, 2H), 1.26 (d, J=6.8 Hz, 6H). $^{13}$C NMR (100 MHz, CDCl$_3$): 145.1, 140.4, 136.6, 132.5, 128.9, 128.4, 126.6, 126.4, 125.3, 124.9, 117.2, 110.5, 53.0, 48.7, 47.8, 43.3, 27.1, 26.5, 25.6, 24.5, 22.3.

Example 22

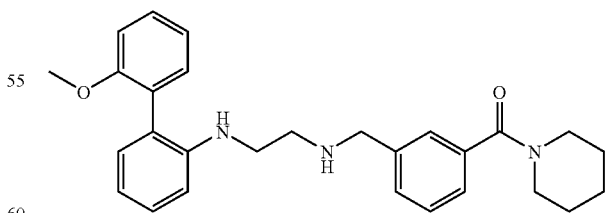

(3-{[2-(2'-Methoxy-biphenyl-2-ylamino)-ethylamino]-methyl}-phenyl)-piperidin-1-yl-methanone To a solution of (3-{[2-(2-bromo-phenylamino)-ethylamino]-methyl}-phenyl)piperidin-1-yl-methanone (Example 17; 0.051 g, 0.12 mmol) and 2-methoxybenzeneboronic acid (0.037 g, 0.25 mmol) in 2 M Na₂CO₃/EtOH/toluene (1:1:4, 6 mL) was added Pd(PPh₃)₄ (0.014 g, 0.012 mmol), and the resulting solution was stirred at reflux for 16 h. The solution was partitioned with EtOAc (20 mL) and satd aqueous NaHCO₃ (20 mL), and the aqueous layer was back-extracted with EtOAc (3×30 mL). The combined organic layers were washed with brine, dried (MgSO₄), filtered, and concentrated under reduced pressure. The crude residue was purified by preparative TLC (10% CH₃OH/CH₂Cl₂) to provide a tan oil (0.0168 g, 28%). MS (ESI): mass calculated for $C_{28}H_{33}N_3O_2$, 443.26; m/z found, 444.2 [M+H]⁺, 466.2 [M+Na]⁺. ¹H NMR (400 MHz, CDCl₃): 7.38-7.22 (m, 7H), 7.08-6.97 (m, 3H), 6.78-6.72 (br s, 2H), 4.15 (br s, 1H), 3.69-3.76 (br m, 4H), 3.68 (s, 3H), 3.29-3.24 (br m, 4H), 2.86-2.76 (m, 2H), 1.75-1.49 (br m, 8H). ¹³C NMR (100 MHz, CDCl₃): 170.2, 156.8, 145.8, 140.4, 136.5, 131.9, 130.7, 129.0, 128.9, 128.6, 128.4, 128.0, 126.4, 125.3, 124.9, 121.1, 116.8, 111.2, 110.5, 55.6, 53.2, 48.7, 47.8, 43.5, 43.6, 26.5, 25.6, 24.5.

Example 23

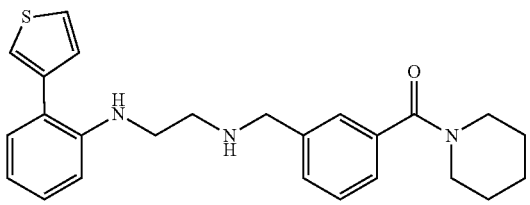

Piperidin-1-yl-(3-{[2-(2-thiophen-3-yl-phenylamino)-ethylamino]-methyl}-phenyl)-methanone The title compound was prepared as in Example 22, substituting 3-thiopheneboronic acid for 2-methoxybenzeneboronic acid. MS (ESI): mass calculated for $C_{25}H_{29}N_3OS$, 419.20; m/z found, 420.2 [M+H]⁺. ¹H NMR (400 MHz, CDCl₃): 7.35-7.16 (m, 10H), 6.76-6.69 (m, 2H), 3.79 (br s, 2H), 3.70 (br s, 2H), 3.30-3.24 (m, 4H), 2.88 (t, J=6.0 Hz, 2H), 1.66-1.48 (br m, 6H).

Example 24

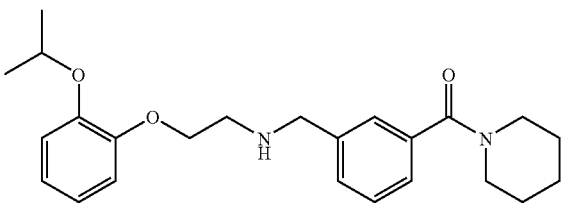

(3-{[2-(2-Isopropoxy-phenoxy)-ethylamino]-methyl}-phenyl)-piperidin-1-yl-methanone A. [2-(2-Isopropoxy-phenoxy)-ethyl]-carbamic acid tert-butyl ester. To a solution of 2-isopropoxy-phenol (0.50 g, 3.3 mmol) in THF (5 mL) was added a suspension of polymer-supported PPh₃ (2.2 g) and (2-hydroxy-ethyl)-carbamic acid tert-butyl ester (0.53 g, 3.3 mmol) in THF (2 mL). The mixture was cooled to 0° C., treated with di-tert-butyl azodicarboxylate (1.1 g, 4.9 mmol), and then allowed to warm to 25° C. over 18 h. The resulting mixture was filtered (diatomaceous earth), and the filtrate was concentrated under reduced pressure. The crude residue was purified by column chromatography (5-20% EtOAc/hexanes) to provide the desired product (0.75 g, 78%). ¹H NMR (400 MHz, CDCl₃): 6.97-6.88 (m, 4H), 4.49 (hept, J=6.1 Hz, 1H), 4.06 (t, J=5.1 Hz, 2H), 3.50-3.46 (m, 2H), 1.45 (s, 9H), 1.37 (d, J=6.1 Hz, 6H).

B. (3-{[2-(2-Isopropoxy-phenoxy)-ethylamino]-methyl}-phenyl)-piperidin-1-yl-methanone. Substitution of [2-(2-isopropoxy-phenoxy)-ethyl]-carbamic acid tert-butyl ester for [2-(2-isopropylamino-phenylamino)-ethyl]-[3-(piperidine-1-carbonyl)-benzyl]-carbamic acid tert-butyl ester in Example 13, step D, provided 2-(2-isopropoxy-phenoxy)-ethylamine. Using the procedure of Example 1, steps D and E, the amine intermediate was then converted to the title compound by its substitution for 2-isopropoxy-phenyl-ethane-1,2-diamine in step E. MS (ESI): mass calculated for $C_{24}H_{32}N_2O_3$, 396.24; m/z found, 397.2 [M+H]⁺. ¹H NMR (400 MHz, CDCl₃): 7.43-7.34 (m, 3H), 7.28-7.26 (m, 1H), 6.96-6.89 (m, 4H), 4.47 (hept, J=6.1 Hz, 1H), 4.13 (t, J=5.04 Hz, 2H), 3.91 (br s, 2H), 3.70 (br s, 2H), 3.34 (br s, 2H), 3.03 (t, J=5.0 Hz, 2H), 1.67 (br s, 4H), 1.51 (br s, 2H), 2.63 (d, J=6.1 Hz, 6H).

Example 25

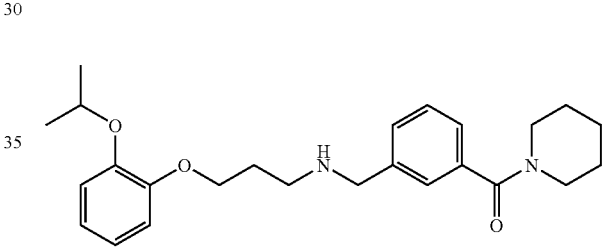

(3-{[3-(2-Isopropoxy-phenoxy)-propylamino]-methyl}-phenyl)-piperidin-1-yl-methanone A. 2-[3-(2-Isopropoxy-phenoxy)-propyl]-isoindole-1,3-dione. To a solution of 2-isopropoxy-phenol (0.50 g, 3.3 mmol) in DMF (5 mL) was added K₂CO₃ (2.3 g, 17 mmol), and the resulting suspension was stirred at 25° C. for 15 min. A solution of 2-(3-bromo-propyl)-isoindole-1,3-dione (0.97 g, 3.6 mmol) in DMF (2 mL) was added, and the reaction mixture was heated to 80° C. for 18 h. The mixture was filtered, and the filtrate was diluted with 1:1 Et₂O/EtOAc (100 mL), washed with H₂O (2×20 mL) then brine (20 mL), dried (MgSO₄), filtered, and concentrated under reduced pressure. The crude residue was purified by column chromatography (5-20% EtOAc/hexanes) to provide the desired product (0.956 g, 87%). ¹H NMR (400 MHz, CDCl₃): 7.87-7.82 (m, 2H), 7.73-7.69 (m, 2H), 6.93-6.86 (m, 4H), 4.46 (hept, J=6.1 Hz, 1H), 4.06 (t, J=6.2 Hz, 2H), 3.92 (t, J=7.1 Hz, 2H), 2.20 (quint, J=6.4 Hz, 2H), 1.33 (d, J=6.1 Hz, 6H).

B. 3-(2-Isopropoxy-phenoxy)-propylamine. To a solution of 2-[3-(2-isopropoxy-phenoxy)-propyl]-isoindole-1,3-dione in EtOH (6 mL) was added hydrazine (0.448 g, 14.0 mmol), and the reaction mixture was heated to 50° C. for 30 min. The solvent was removed under reduced pressure, and the crude residue was partitioned between CH₂Cl₂ (50 mL) and H₂O (50 mL). The aqueous layer was extracted with $CH_2Cl_2$ (3×50 mL), and the combined organic layers were washed with brine, dried ($MgSO_4$), filtered, and concentrated under reduced pressure. The resulting residue was purified by column chromatography (20-50% EtOAc/hexanes) to provide the desired product (0.267 g, 45%). MS (ESI): mass calculated for $C_{12}H_{19}NO_2$, 209.29; m/z found, 210.2 $[M+H]^+$. $^1H$ NMR (400 MHz, $CDCl_3$): 6.91-6.83 (m, 4H), 4.46 (hept, J=6.1 Hz, 1H), 4.07 (t, J=5.9 Hz, 2H), 2.97 (t, J=6.5 Hz, 2H), 1.99 (quint, J=6.2 Hz, 2H), 1.32 (d, J=6.1 Hz, 6H).

C. (3-{[3-(2-Isopropoxy-phenoxy)-propylamino]-methyl}-phenyl)-piperidin-1-yl-methanone. The title compound was prepared as in Example 1 steps D and E substituting 3-(2-isopropoxy-phenoxy)-propylamine for $N^1$-(2-isopropoxy-phenyl)-ethane-1,2-diamine. MS (ESI): mass calculated for $C_{25}H_{34}N_2O_3$, 410.26; m/z found, 411.4 $[M+H]^+$. $^1H$ NMR (400 MHz, $CDCl_3$): 7.41-7.38 (m, 2H), 7.33 (t, J=7.5 Hz, 1H), 7.27-7.25 (m, 1H), 6.95-6.85 (m, 4H), 4.45 (hept, J=6.1 Hz, 1H), 4.08 (t, J=6.0 Hz, 2H), 3.87 (br s, 2H), 3.69 (br s, 2H), 3.31 (br s, 2H), 2.87 (t, J=6.6 Hz, 2H), 2.06-2.00 (m, 2H), 1.65 (br s, 4H), 1.48 (br s, 2H), 1.31 (d, J=6.1 Hz, 6H).

Example 26

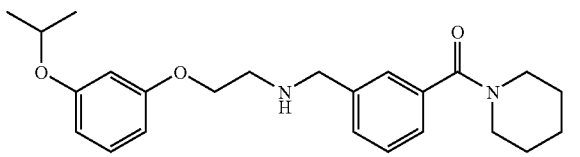

(3-{[2-(3-Isopropoxy-phenoxy)-ethylamino]-methyl}-phenyl)-piperidin-1-yl-methanone A. Benzoic acid 3-(2-amino-ethoxy)-phenyl ester. To a solution cooled to 0° C. of resorcinol monobenzoate (3.0 g, 14 mmol) in THF (70 mL) was added $PPh_3$ (7.35 g, 28.0 mmol) and (2-hydroxy-ethyl)-carbamic acid tert-butyl ester (2.3 g, 14 mmol). Diisopropyl azodicarboxylate (4.25 g, 21.0 mmol) was added, and the mixture was stirred at 25° C. for 14 h. The solvent was removed under reduced pressure. The residue was treated with $Et_2O$ (100 mL), and the mixture was cooled to 0° C. for 30 min. The precipitate that formed was removed by filtration, and the filtrate was concentrated under reduced pressure. The crude residue was dissolved in 1:1 $TFA/CH_2Cl_2$ (10 mL), and the solution was stirred at 25° C. for 3 h. The solvent was removed under reduced pressure, and the residue was purified by column chromatography (10% $CH_3OH/CH_2Cl_2$) to provide the desired ester (1.3 g, 37% yield over two steps). MS (ESI): mass calculated for $C_{15}H_{15}NO_3$, 257.1; m/z found, 258.1 $[M+H]^+$. $^1H$ NMR (400 MHz, $CDCl_3$): 8.10-8.08 (m, 2H), 7.82 (br s, 2H), 7.60-7.56 (m, 1H), 7.43 (t, J=7.7 Hz, 2H), 7.22 (t, J=8.2 Hz, 1H), 6.77-6.69 (m, 3H), 4.06 (br s, 2H), 3.22 (br s, 2H).

B. Benzoic acid 3-{2-[3-(piperidine-1-carbonyl)-benzylamino]-ethoxy}-phenyl ester. The title compound was prepared as in Example 1, steps D and E, substituting benzoic acid 3-(2-amino-ethoxy)-phenyl ester for $N^1$-(2-isopropoxy-phenyl)-ethane-1,2-diamine in step E. MS (ESI): mass calculated for $C_{28}H_{30}N_2O_4$, 458.22; m/z found, 459.2 $[M+H]^+$, 481.2 $[M+Na]^+$.

C. (3-{[2-(3-Isopropoxy-phenoxy)-ethylamino]-methyl}-phenyl)-piperidin-1-yl-methanone. To a solution of benzoic acid 3-{2-[3-(piperidine-1-carbonyl)benzylamino]-ethoxy}-phenyl ester (0.046 g, 0.10 mmol) in THF (10 mL) was added NaOH (4 M, 1 mL), and the resulting solution was stirred at 25° C. for 4 h. The solvent was removed under reduced pressure, and the crude residue was partitioned between EtOAc (40 mL) and 1 N HCl (50 mL). The aqueous layer was back-extracted with EtOAc (3×50 mL), and the combined organic layers were washed with brine, dried ($Na_2SO_4$), filtered, and concentrated under reduced pressure. Potassium carbonate (0.035 g, 0.25 mmol) was added to a solution of the residue in DMF (0.05 mL), and the resulting suspension was stirred at 25° C. for 30 min. 2-Bromopropane (0.018 g, 0.15 mmol) was added, and the mixture was stirred at 25° C. for 14 h. The solvent was removed under reduced pressure, and the crude residue was partitioned between EtOAc (5 mL) and $H_2O$ (5 mL). The aqueous layer was back-extracted with EtOAc (20 mL) and $CH_2Cl_2$ (3×20 mL), and the combined organic layers were washed with brine, dried ($MgSO_4$), filtered, and concentrated under reduced pressure. The residue was purified by preparative TLC (10% $CH_3OH/CH_2Cl_2$) to provide the desired product (0.010 g, 25%). MS (ESI): mass calculated for $C_{24}H_{32}N_2O_3$, 396.24; m/z found, 397.1 $[M+H]^+$. $^1H$ NMR (400 MHz, $CDCl_3$): 7.42-7.34 (m, 3H), 7.28-7.15 (m, 1H), 7.19-7.15 (m, 1H), 6.51-6.45 (m, 3H), 4.52 (hept, J=6.1 Hz, 1H), 4.08 (t, J=5.1 Hz, 2H), 3.92 (s, 2H), 3.70 (br s, 2H), 3.33 (br s, 2H), 3.04 (t, J=5.1 Hz, 2H), 1.67-1.45 (m, 6H), 1.32 (d, J=6.1 Hz, 6H).

Example 27

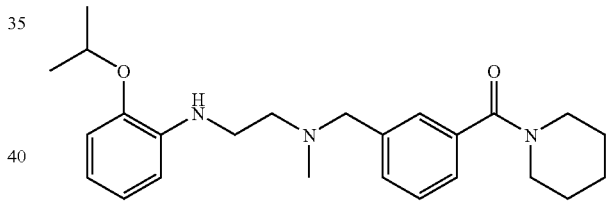

[3-({[2-(2-Isopropoxy-phenylamino)-ethyl]-methyl-amino}-methyl)-phenyl]-piperidinyl-methanone To a solution of (3-{[2-(2-isopropoxy-phenylamino)-ethylamino]-methyl}-phenyl)-piperidin-1-yl-methanone (Example 1; 0.032 g, 0.081 mmol) in DMF (0.8 mL) was added $K_2CO_3$ (0.022 g, 0.16 mmol) and iodomethane (0.03 g, 0.2 mmol), and the resulting suspension was stirred at 25° C. for 45 min. The suspension was partitioned with EtOAc (20 mL) and $H_2O$ (20 mL), and the organic layer was washed with brine (20 mL), dried ($Na_2SO_4$), filtered, and concentrated under reduced pressure. The crude residue was purified by preparative TLC (2% $CH_3OH/CH_2Cl_2$) to provide a colorless oil (0.015 g, 47%). MS (ESI): mass calculated for $C_{26}H_{35}N_3O_2$, 409.27; m/z found, 410.5 $[M+H]^+$, 432.4 $[M+Na]^+$. $^1H$ NMR ($CDCl_3$, 400 MHz): 7.46 (d, J=7.6 Hz, 1H), 7.36-7.31 (m, 2H), 7.27-7.25 (m, 1H), 6.84 (dt, J=7.8, 1.3 Hz, 1H), 6.78 (dt, J=7.8, 1.3 Hz, 1H), 6.63 (dt, J=7.8, 1.6 Hz, 1H), 6.58 (dt, J=7.8, 1.6 Hz, 1H), 4.53 (hept, J=6.1 Hz, 1H), 3.70 (br s, 2H), 3.60 (br s, 2H), 3.31 (br s, 2H), 3.20 (t, J=6.1 Hz, 2H), 2.73 (t, J=6.1 Hz, 2H), 2.20 (s, 3H), 1.62-1.46 (m, 6H), 1.37 (d, J=6.1 Hz, 6H).

Example 28

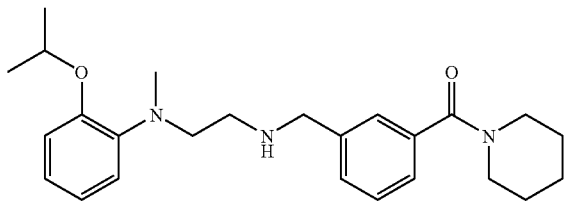

[3-({2-[(2-Isopropoxy-phenyl)-methyl-amino]-ethylamino}-methyl)-phenyl]-piperidinyl-methanone A. [2-(2-Isopropoxy-phenylamino)-ethyl]-[3-(piperidine-1-carbonyl)-benzyl]-carbamic acid tert-butyl ester. To a solution of (3-{[2-(2-isopropoxy-phenylamino)-ethylamino]-methyl}-phenyl)-piperidin-1-yl-methanone (Example 1; 0.133 g, 0.336 mmol) in $CH_2Cl_2$ (3.5 mL) was added di-tert-butyl dicarbonate (0.073 g, 0.33 mmol), and the resulting solution was stirred at 25° C. for 45 min. The solvent was removed under reduced pressure, and the crude residue was purified by column chromatography (0-5% $CH_3OH/CH_2Cl_2$) to provide a colorless oil (0.144 g, 86%). $^1$H NMR ($CDCl_3$, 400 MHz): 7.35-7.32 (m, 1H), 7.28-7.22 (m, 4H), 6.83-6.76 (m, 2H), 6.64-6.57 (m, 2H), 4.55-4.45 (m, 3H), 3.68 (br s, 2H), 3.50 (br s, 1H), 3.37 (br s, 1H), 3.31-3.26 (m, 5H), 1.66-1.62 (m, 6H), 1.50 (br s, 9H), 1.34 (d, J=6.1 Hz, 6H).

B. {2-[(2-Isopropoxy-phenyl)-methyl-amino]-ethyl}-[3-(piperidine-1-carbonyl)benzyl]-carbamic acid tert-butyl ester. To a solution of [2-(2-isopropoxy-phenylamino)-ethyl]-[3-(piperidine-1-carbonyl)-benzyl]-carbamic acid tert-butyl ester (0.077 g, 0.16 mmol) in DMF (1.6 mL) cooled to 0° C. was added NaH (0.062 g, 1.6 mmol), and the resulting suspension was allowed to warm to 25° C. over 30 min. The suspension was cooled to 0° C., and iodomethane (0.22 g, 1.6 mmol) was added. This suspension was allowed to warm to 25° C. over 4 h and then was partitioned with EtOAc (25 mL) and $H_2O$ (25 mL). The aqueous layer was back-extracted with EtOAc (25 mL). The combined organic layers were washed with brine (25 mL), dried ($Na_2SO_4$) and filtered, and the filtrate was concentrated under reduced pressure. The crude residue was purified by preparative TLC (5% $CH_3OH/CH_2Cl_2$) to provide a colorless oil (0.028 g, 35%). MS (ESI): mass calculated for $C_{30}H_{43}N_3O_4$, 509.33; m/z found, 510.5 $[M+H]^+$.

C. [3-({2-[(2-Isopropoxy-phenyl)-methyl-amino]-ethylamino}-methyl)-phenyl]-piperidin-1-yl-methanone. The title compound was prepared as in Example 13, step D, substituting {2-[(2-isopropoxy-phenyl)-methyl-amino]-ethyl}-[3-(piperidine-1-carbonyl)-benzyl]-carbamic acid tert-butyl ester for 2-(2-isopropylamino-phenylamino)-ethyl]-[3-(piperidine-1-carbonyl)-benzyl]-carbamic acid tert-butyl ester. MS (ESI): mass calculated for $C_{25}H_{35}N_3O_2$, 409.27; m/z found, 410.4 $[M+H]^+$, 432.4 $[M+Na]^+$. $^1$H NMR (400 MHz, $CDCl_3$): 7.44-7.33 (m, 4H), 7.06-7.00 (m, 2H), 6.93-6.88 (m, 2H), 4.55 (hept, J=6.0 Hz, 1H), 4.02 (s, 2H), 3.69 (br s, 2H), 3.31 (br s, 2H), 3.19 (t, J=5.9 Hz, 2H), 2.90 (t, J=5.9 Hz, 2H), 2.70 (s, 3H), 1.66 (br s, 4H), 1.49 (br s, 2H), 1.29 (d, J=6.0 Hz, 6H).

Example 29

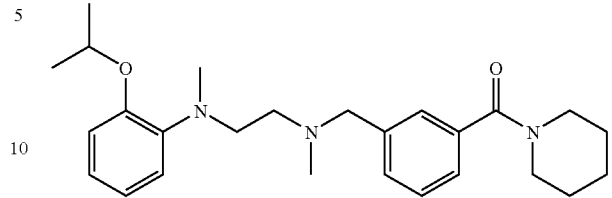

{3-[({2-[(2-Isopropoxy-phenyl)-methyl-amino]-ethyl}-methyl-amino)-methyl]-phenyl}-piperidin-1-yl-methanone The title compound was prepared as in Example 27 substituting [3-({2-[(2-isopropoxy-phenyl)-methyl-amino]-ethylamino}-methyl)-phenyl]-piperidin-1-yl-methanone for (3-{[2-(2-isopropoxy-phenylamino)-ethylamino]-methyl}-phenyl)piperidin-1-yl-methanone. MS (ESI): mass calculated for $C_{26}H_{37}N_3O_2$, 323.29; m/z found, 324.5 $[M+H]^+$. $^1$H NMR (400 MHz, $CDCl_3$): 7.71 (dd, J=5.9, 3.3 Hz, 1H), 7.53 (dd, J=5.9, 3.3 Hz, 1H), 7.30-7.33 (m, 2H), 6.93-6.82 (m, 4H), 4.59 (hept, J=6.1 Hz, 1H), 3.70 (br s, 2H), 3.52 (s, 2H), 3.31 (br s, 2H), 3.25 (t, J=7.3 Hz, 2H), 2.80 (s, 3H), 2.63 (t, J=7.3 Hz, 2H), 2.19 (s, 3H), 1.67 (br s, 6H), 1.35 (d, J=6.1 Hz, 6H).

Example 30

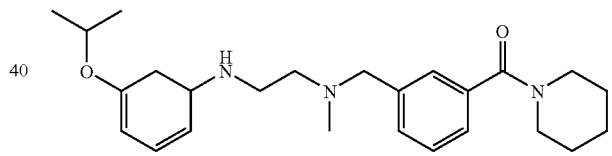

[3-({[2-(3-Isopropoxy-phenylamino)-ethyl]-methyl-amino}-methyl)-phenyl]-piperidin-1-yl-methanone To a solution of (3-{[2-(3-isopropoxy-phenylamino)-ethylamino]-methyl}-phenyl)-piperidin-1-yl-methanone (Example 10; 0.048 g, 0.12 mmol) in $CH_3CN$ (10 mL) was added a solution of formaldehyde (0.0029 g, 0.097 mmol) in $CH_3CN$ (5 mL), followed by sodium cyanoborohydride (0.006 g, 0.1 mmol) and acetic acid (2 drops), and the resulting solution was stirred at 25° C. for 15 h. The solution was treated with aqueous satd $NaHCO_3$ (20 mL), $H_2O$ (20 mL) and EtOAc (30 mL). The aqueous layer was back-extracted with EtOAc (3×40 mL), and the combined organic layers were washed with brine (40 mL), dried ($MgSO_4$) and filtered. The filtrate was concentrated under reduced pressure. The crude residue was purified by preparative TLC (5% $CH_3OH/CH_2Cl_2$) to provide a tan oil (0.0063 g, 13%). MS (ESI): mass calculated for $C_{25}H_{35}N_3O_2$, 409.27; m/z found, 410.2 $[M+H]^+$. $^1$H NMR (400 MHz, $CDCl_3$): 7.39-7.26 (m, 4H), 7.04 (t, J=8.0 Hz, 1H), 6.26-6.16 (m, 3H), 4.15 (hept, J=6.0

Hz, 1H), 3.71-3.61 (m, 4H), 3.31-3.20 (m, 4H), 2.72 (br s, 2H), 2.26 (br s, 2H), 1.66-1.50 (m, 8H), 1.32 (d, J=6.0 Hz, 6H).

Example 31

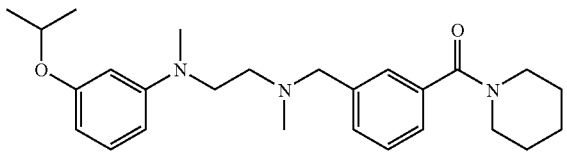

{3-[({2-[(3-Isopropoxy-phenyl)-methyl-amino]-ethyl}-methyl-amino)-methyl]-phenyl}-piperidin-1-yl-methanone To a solution of (3-{[2-(3-isopropoxy-phenylamino)-ethylamino]-methyl}-phenyl)piperidin-1-yl-methanone (Example 10; 0.048 g, 0.12 mmol) in $CH_3CN$ (10 mL) was added a solution of formaldehyde (0.040 g, 1.3 mmol) in $CH_3CN$ (5 mL), sodium cyanoborohydride (0.080 g, 1.3 mmol) and acetic acid (2 drops), and the resulting solution was stirred at 25° C. for 15 h. The reaction mixture was treated with aqueous satd $NaHCO_3$ (20 mL), $H_2O$ (20 mL) and EtOAc (30 mL). The aqueous layer was back-extracted with EtOAc (3×40 mL), and the combined organic layers were washed with brine (40 mL), dried ($MgSO_4$), and filtered. The filtrate was concentrated under reduced pressure. The crude residue was purified by preparative TLC (5% $CH_3OH/CH_2Cl_2$) to provide a tan oil (8.7 mg, 18%). MS (ESI): mass calculated for $C_{26}H_{37}N_3O_2$, 423.29; m/z found, 424.5 [M+H]$^+$. $^1$H NMR (400 MHz, CDCl$_3$): 7.42-7.26 (m, 4H), 7.08 (t, J=8.1 Hz, 1H), 6.29-6.21 (m, 3H), 4.52 (hept, J=6.0 Hz, 1H), 3.70-3.31 (br m, 8H), 2.92 (br s, 3H), 2.68 (br s, 2H), 2.33 (br s, 3H), 1.67-1.50 (br m, 8H), 1.32 (d, J=6.0 Hz, 6H).

Example 32

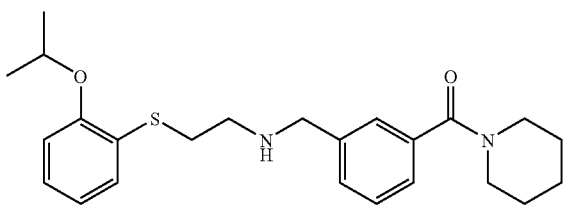

(3-{[2-(2-Isopropoxy-phenylsulfanyl)-ethylamino]-methyl}-phenyl)-piperidin-1-yl-methanone A. 2-[2-(2-Hydroxy-phenylsulfanyl)-ethyl]-isoindole-1,3-dione. To a solution of 2-mercaptophenol (1.0 g, 7.9 mmol) in DMF (80 mL) was added 2-(2-bromoethyl)-isoindole-1,3-dione (1.8 g, 7.1 mmol) followed by $K_2CO_3$ (1.1 g, 7.9 mmol), and the suspension was stirred at 25° C. for 2 h. The suspension was then diluted with $H_2O$ (200 mL), and the resulting mixture was extracted with EtOAc (2×100 mL). The combined organic layers were washed with $H_2O$ (2×100 mL), dried ($Na_2SO_4$) and filtered, and the filtrate was concentrated under reduced pressure. The crude oil was purified by column chromatography (0-30% EtOAc/hexanes) to provide a light yellow solid (1.8 g, 76%). MS (ESI): mass calculated for $C_{16}H_{13}NO_3S$, 299.06; m/z found, 332.4 [M+Na]$^+$. $^1$H NMR (400 MHz, CDCl$_3$): 7.85 (dd, J=5.4, 3.0 Hz, 2H), 7.73 (dd, J=5.4, 3.0 Hz, 2H), 7.56 (d, J=8.0 Hz, 1H), 7.26-7.21 (m, 1H), 7.00 (s, 1H), 6.95 (dd, J=7.9, 1.3 Hz, 1H), 6.88 (dt, J=7.9, 1.3 Hz, 1H), 3.90 (t, J=6.2 Hz, 2H), 3.05 (t, J=6.2 Hz, 2H).

B. 2-[2-(2-Isopropoxy-phenylsulfanyl)-ethyl]-isoindole-1,3-dione. The title intermediate was prepared as in Example 1, step A, substituting 2-[2-(2-hydroxy-phenylsulfanyl)-ethyl]-isoindole-1,3-dione for 2-nitrophenol. MS (ESI): mass calculated for $C_{19}H_{19}NO_3S$, 341.11; m/z found, 342.2 [M+H]$^+$, 364.1 [M+Na]$^+$. $^1$H NMR (400 MHz, CDCl$_3$): 7.81 (dd, J=5.6, 3.1 Hz, 2H), 7.70 (dd, J=5.6, 3.1 Hz, 2H), 7.53 (dd, J=7.8, 1.7 Hz, 1H), 7.14-7.09 (m, 1H), 6.89-6.81 (m, 2H), 4.58 (hept, J=6.0 Hz, 1H), 3.91 (t, J=7.3 Hz, 2H), 3.21 (t, J=7.3 Hz, 2H), 1.38 (d, J=6.0 Hz, 6H).

C. 2-(2-Isopropoxy-phenylsulfanyl)-ethylamine. The title intermediate was prepared as in Example 25, step B, substituting 2-[2-(2-isopropoxy-phenylsulfanyl)-ethyl]-isoindole-1,3-dione for 2-[3-(2-isopropoxy-phenoxy)-propyl]-isoindole-1,3-dione. $^1$H NMR (400 MHz, CDCl$_3$): 7.30 (dd, J=7.6, 1.5 Hz, 1H), 7.15 (dt, J=7.6, 1.5 Hz, 1H), 6.90-6.84 (m, 2H), 4.57 (hept, J=6.2 Hz, 1H), 2.96 (t, J=5.9 Hz, 2H), 2.86 (t, J=5.9 Hz, 2H), 1.52 (br s, 2H), 1.37 (d, J=6.2 Hz, 6H).

D. (3-{[2-(2-Isopropoxy-phenylsulfanyl)-ethylamino]-methyl}-phenyl)-piperidin-1-yl-methanone. The title compound was prepared as in Example 1, steps D and E, substituting 2-(2-isopropoxy-phenylsulfanyl)-ethylamine for N$^1$-(2-isopropoxy-phenyl)-ethane-1,2-diamine in step D. MS (ESI): mass calculated for $C_{24}H_{32}N_2O_2S$, 412.22; m/z found, 413.2 [M+H]$^+$, 435.2 [M+Na]$^+$. $^1$H NMR (400 MHz, CDCl$_3$): 7.35-7.23 (m, 5H), 7.15 (dt, J=7.7, 1.5 Hz, 1H), 6.89-6.84 (m, 2H), 4.57 (hept, J=6.2 Hz, 1H), 3.80 (s, 2H), 3.70 (br s, 2H), 3.31 (br s, 2H), 3.06 (t, J=6.4 Hz, 2H), 2.84 (t, J=6.4 Hz, 2H), 1.94 (br s, 1H), 1.66 (br s, 4H), 1.49 (br s, 2H), 1.36 (d, J=6.2 Hz, 6H).

Example 33

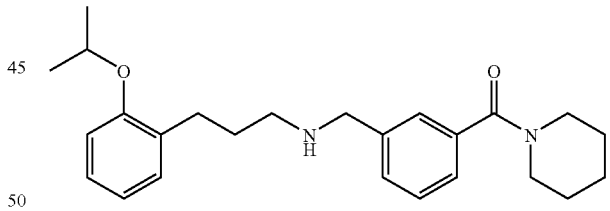

(3-{[3-(2-Isopropoxy-phenyl)-propylamino]-methyl}-phenyl)-piperidin-1-yl-methanone A. 3-(2-Isopropoxy-phenyl)-propionic acid isopropyl ester. To a solution of 3-(2-hydroxy-phenyl)-propionic acid (0.94 g, 5.7 mmol) in DMF (11.3 mL) was added $K_2CO_3$ (3.9 g, 28 mmol) and 2-iodopropane (1.9 g, 11 mmol), and the resulting suspension was stirred at 25° C. for 15 h. The suspension was partitioned with EtOAc (75 mL) and $H_2O$ (50 mL), and the organic layer was washed with 1 M NaOH (2×50 mL) then brine (50 mL), dried ($Na_2SO_4$), and filtered. The filtrate was concentrated under reduced pressure yielding a crude oil, which was purified by column chromatography (0-30% EtOAc/hexanes) to provide a colorless oil (0.51 g, 36%). $^1$H NMR (400 MHz, CDCl$_3$): 7.17-7.12 (m, 2H), 6.85-

6.81 (m, 2H), 4.99 (hept, J=6.3 Hz, 1H), 4.56 (hept, J=6.1 Hz, 1H), 2.91 (t, J=7.8 Hz, 2H), 2.57 (t, J=7.8 Hz, 2H), 1.34 (d, J=6.1 Hz, 6H), 1.20 (d, J=6.3 Hz, 6H).

B. 3-(2-Isopropoxy-phenyl)-propionamide. Ammonia gas was bubbled through a −78° C. solution of 3-(2-isopropoxy-phenyl)-propionic acid isopropyl ester (0.19 g, 0.76 mmol) in CH₃OH (6.0 mL) for 5 min. The reaction tube was sealed, and the solution was allowed to warm to 25° C., and stirred for 24 h. The solution was then cooled to −78° C., and the tube was unsealed. The solution was concentrated under reduced pressure. The crude residue was purified by column chromatography (0-15% CH₃OH/CH₂Cl₂) to provide a white solid (0.10 g, 69%). $^1$H NMR (400 MHz, CDCl₃): 7.19-7.15 (m, 2H), 6.88-6.84 (m, 2H), 5.47 (br s, 1H), 5.27 (br s, 1H), 4.58 (hept, J=6.1 Hz, 1H), 2.94 (t, J=7.7 Hz, 2H), 2.57 (t, J=7.7 Hz, 2H), 1.35 (d, J=6.0 Hz, 6H).

C. 3-(2-Isopropoxy-phenyl)-propylamine. To a solution of 3-(2-isopropoxy-phenyl)-propionamide (0.070 g, 0.34 mmol) in THF (6.8 mL) was added lithium aluminum hydride (0.051 g, 1.34 mmol), and the resulting suspension was stirred at reflux for 2 h. The suspension was cooled to 0° C. and treated sequentially with H₂O (0.10 mL), 10% NaOH (0.10 mL) and H₂O (0.15 mL). The resulting solid was filtered off and washed with EtOAc (50 mL). The combined filtrates were dried (Na₂SO₄), filtered, and concentrated under reduced pressure to provide a colorless oil (0.050 g, 65%). MS (ESI): mass calculated for C₁₂H₁₉NO, 193.15; m/z found, 194.2 [M+H]⁺.

D. (3-{[3-(2-Isopropoxy-phenyl)-propylamino]-methyl}-phenyl)-piperidin methanone. The title compound was prepared as in Example 1, steps D and E, substituting 3-(2-isopropoxy-phenyl)-propylamine for N¹-(2-isopropoxy-phenyl)-ethane-1,2-diamine in step E. MS (ESI): mass calculated for C₂₅H₃₄N₂O₂, 394.26; m/z found, 395.3 [M+H]⁺, 417.3 [M+Na]⁺. $^1$H NMR (400 MHz, CDCl₃): 7.38-7.32 (m, 3H), 7.27-7.24 (m, 1H), 7.15-7.10 (m, 2H), 6.86-6.82 (m, 2H), 4.53 (hept, J=6.1 Hz, 1H), 3.81 (s, 2H), 3.70 (br s, 2H), 3.32 (br s, 2H), 2.68-2.62 (m, 4H), 1.85-1.77 (m, 2H), 1.67 (br s, 4H), 1.50 (br s, 2H), 1.32 (d, J=6.1 Hz, 6H).

Example 34

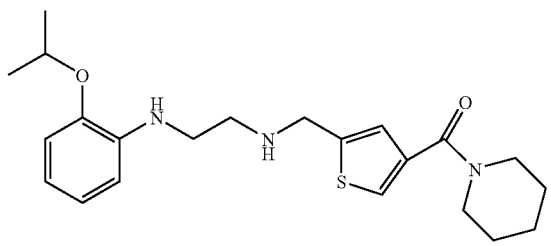

(5-{[2-(2-Isopropoxy-phenylamino)-ethylamino]-methyl}-thiophen-3-yl)-piperidin-1-yl-Methanone A. 4-(Piperidine-1-carbonyl)-thiophene-2-carbaldehyde. The title intermediate was prepared as in Example 1, step D, substituting 5-formyl-thiophene-3-carboxylic acid for 3-formyl-benzoic acid. MS (ESI): mass calculated for C₁₁H₁₃NO₂S, 223.29; m/z found, 224.0 [M+H]⁺, 246.0 [M+Na]⁺. $^1$H NMR (400 MHz, CDCl₃): 9.92 (s, 1H), 7.83 (s, 1H), 7.83 (s, 1H), 3.68 (br s, 2H), 3.50 (br s, 2H), 1.71 (br s, 4H), 1.63 (br s, 2H).

B. (5-{[2-(2-Isopropoxy-phenylamino)-ethylamino]-methyl}-thiophen-3-yl)piperidin-1-yl-methanone. The title compound was prepared as in Example 1, step E, substituting 4-(piperidine-1-carbonyl)-thiophene-2-carbaldehyde for 3-(piperidine-1-carbonyl)-benzaldehyde. MS (ESI): mass calculated for C₂₂H₃₁N₃O₂S, 401.21; m/z found, 402.2 [M+H]⁺, 424.2 [M+Na]⁺. $^1$H NMR (400 MHz, CDCl₃): 7.32 (d, J=1.4 Hz, 1H), 6.97 (d, J=1.4 Hz, 1H), 6.84 (dt, J=7.8, 1.3 Hz, 1H), 6.78 (dd, J=8.4, 1.1 Hz, 1H), 6.65-6.60 (m, 2H), 4.62 (br s, 1H), 4.52 (hept, J=6.2 Hz, 1H), 3.99 (s, 2H), 3.56 (br s, 4H), 3.25 (t, J=5.7 Hz, 2H), 2.94 (t, J=5.7 Hz, 2H), 1.66 (br s, 3H), 1.57 (br s, 3H), 1.36 (d, J=6.2 Hz, 6H).

Example 35

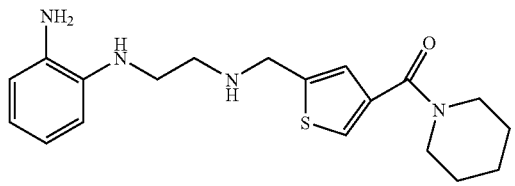

(5-{[2-(2-Amino-phenylamino)-ethylamino]-methyl}-thiophen-3-yl)-piperidin-1-yl-methanone A. (5-{[2-(2-Nitro-phenylamino)-ethylamino]-methyl}-thiophen-3-yl)-piperidin-1-yl-methanone. The title intermediate was prepared as in Example 1, step E, using 4-(piperidine-1-carbonyl)-thiophene-2-carbaldehyde and N¹-(2-nitrophenyl)-ethane-1,2-diamine. MS (ESI): mass calculated for C₁₉H₂₄N₄O₃S, 388.49; m/z found, 389.1 [M+H]⁺, 411.1 [M+Na]⁺. $^1$H NMR (400 MHz, CDCl₃): 8.33 (br s, 1H), 8.17 (dd, J=8.6, 1.5 Hz, 1H), 7.45-7.41 (m, 1H), 7.34 (d, J=1.2 Hz, 1H), 7.01 (d, J=1.2 Hz, 1H), 6.58 (d, J=7.8 Hz, 1H), 6.67-6.62 (m, 1H), 4.04 (s, 2H), 3.57 (br s, 4H), 3.42 (dd, J=6.0, 5.5 Hz, 1H), 3.03 (t, J=6.0 Hz, 2H), 1.67 (br s, 4H), 1.60 (br s, 2H).

B. [2-(2-Nitro-phenylamino)-ethyl]-[4-(piperidine-1-carbonyl)-thiophen-2-ylmethyl]-carbamic acid tert-butyl ester. The title intermediate was prepared as in Example 13, step A, substituting (5-{[2-(2-nitro-phenylamino)-ethylamino]-methyl}-thiophen-3-yl)-piperidin-1-yl-methanone for (3-{[2-(2-nitro-phenylamino) -ethylamino]-methyl}-phenyl)-piperidin-1-yl-methanone. $^1$H NMR (400 MHz, CDCl₃): 8.21-8.11 (m, 2H), 7.44 (t, J=7.6 Hz, 1H), 7.35 (d, J=1.0 Hz, 1H), 7.02-6.84 (m, 2H), 6.66 (t, J=7.7 Hz, 1H), 4.59-4.55 (m, 2H), 3.62-3.44 (m, 8H), 1.08 (br s, 4H), 1.58 (br s, 2H), 1.52 (br s, 9H).

C. [2-(2-Amino-phenylamino)-ethyl]-[4-(piperidine-1-carbonyl)-thiophen-2-ylmethyl]-carbamic acid tert-butyl ester. The title intermediate was prepared as in Example 13, step B, substituting [2-(2-nitro-phenylamino)-ethyl]-[4-(piperidine-1-carbonyl)-thiophen-2-ylmethyl]-carbamic acid tert-butyl ester for [2-(2-nitro-phenylamino)-ethyl]-[3-(piperidine-1-carbonyl)-benzyl]-carbamic acid tert-butyl ester. $^1$H NMR (400 MHz, CDCl₃): 7.33 (br s, 1H), 6.90 (br s, 1H), 6.78-6.74 (m, 1H), 6.68-6.55 (m, 3H), 4.57-4.49 (m, 2H), 3.68-3.39 (m, 6H), 3.25 (br s, 2H), 1.65 (br s, 2H), 1.55 (br s, 4H), 1.50 (br s, 9H).

D. (5-{[2-(2-Amino-phenylamino)-ethylamino]-methyl}-thiophen-3-yl)-piperidin-1-yl-methanone. The title compound was prepared as in Example 13, step D, substituting [2-(2-amino-phenylamino)-ethyl]-[4-(piperidine-1-carbonyl)thiophen-2-ylmethyl]-carbamic acid tert-butyl ester for

[2-(2-isopropylamino-phenylamino) -ethyl]-[3-(piperidine-1-carbonyl)-benzyl]-carbamic acid tert-butyl ester. $^1$H NMR (400 MHz, CDCl$_3$): 7.32 (d, J=1.5 Hz, 1H), 6.99 (d, J=1.5 Hz, 1H), 6.82-6.77 (m, 1H), 6.72-6.64 (m, 3H), 3.98 (s, 2H), 3.50 (br s, 4H), 3.21 (t, J=5.7 Hz, 2H), 2.96 (t, J=5.7 Hz, 2H), 1.67 (br s, 2H), 1.58 (br s, 4H).

Example 36

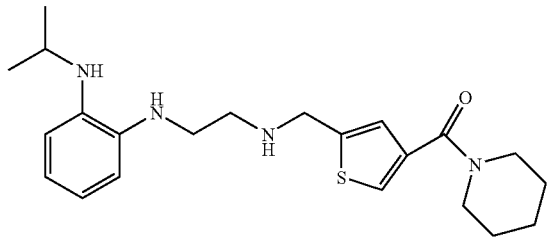

(5-{[2-(2-Isopropylamino-phenylamino)-ethylamino]-methyl}-thiophen-3-yl)-piperidinyl-methanone The title compound was prepared as in Example 13, steps C and D, substituting [2-(2-amino-phenylamino)-ethyl]-[4-(piperidine-1-carbonyl)thiophen-2-ylmethyl]-carbamic acid tert-butyl ester (Example 35, step C) for [2-(2-amino-phenylamino)-ethyl]-[3-(piperidine-1-carbonyl)-benzyl]-carbamic acid tert-butyl ester in step C.

A. [2-(2-Isopropylamino-phenylamino)-ethyl]-[4-(piperidine-1-carbonyl)thiophen-2-ylmethyl]-carbamic acid tert-butyl ester. $^1$H NMR (400 MHz, CDCl$_3$): 7.34 (d, J=1.5 Hz, 1H), 6.97 (br s, 1H), 6.77-6.57 (m, 4H), 4.54-4.50 (m, 2H), 3.62-3.43 (s, 8H), 3.25 (t, J=6.1 Hz, 2H), 1.66 (br s, 2H), 1.57 (br s, 4H), 1.51 (br s, 9H), 1.22 (d, J=6.1 Hz, 6H).

B. (5-{[2-(2-Isopropylamino-phenylamino)-ethylamino]-methyl}-thiophen-3-yl)piperidin-1-yl-methanone. MS (ESI): mass calculated for C$_{22}$H$_{32}$N$_4$OS, 400.58; m/z found, 401.2 [M+H]$^+$, 423.2 [M+Na]$^+$. $^1$H NMR (400 MHz, CDCl$_3$): 7.34 (d, J=1.5 Hz, 1H), 6.99 (br s, 1H), 6.80-6.73 (m, 2H), 6.69-6.66 (m, 2H), 4.01 (s, 2H), 3.66-3.48 (m, 5H), 3.21-3.18 (m, 2H), 2.99-2.96 (m, 2H), 1.68 (br s, 2H), 1.59 (br s, 4H), 1.25 (d, J=6.2 Hz, 6H).

Example 37

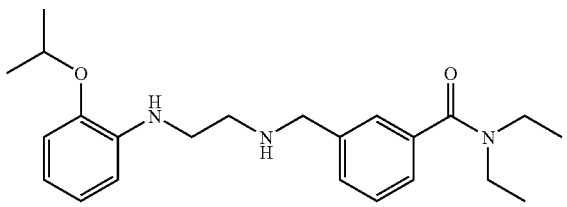

N,N-Diethyl-3-{[2-(2-isopropoxy-phenylamino)-ethylamino]-methyl}-benzamide

A. 3-{[2-(2-Isopropoxy-phenylamino)-ethylamino]-methyl}-benzoic acid methyl ester. To a solution of N$^1$-(2-isopropoxy-phenyl)-ethane-1,2-diamine (Example 1, step C, 0.432 g, 2.22 mmol) and 3-formyl-benzoic acid methyl ester (0.33 g, 2.0 mmol) in 1,2-dichloroethane (22 mL) was added sodium triacetoxyborohydride (0.6 g, 3 mmol), and the resulting suspension was stirred at 25° C. for 2 h. The resulting solution was partitioned with EtOAc (50 mL), H$_2$O (20 mL) and 1 N NaOH (30 mL), and the aqueous layer was back-extracted with EtOAc (3×50 mL). The combined organic layers were washed with brine, dried (MgSO$_4$), filtered, and concentrated under reduced pressure. The crude residue was purified by column chromatography (5-10% CH$_3$OH/CH$_2$Cl$_2$) to provide an orange oil (0.32 g, 46%). MS (ESI): mass calculated for C$_{20}$H$_{26}$N$_2$O$_3$, 342.19; m/z found, 343.2 [M+H]$^+$, 365.2 [M+Na]$^+$. $^1$H NMR (400 MHz, CDCl$_3$): 7.99 (br s, 1H), 7.94-7.91 (m, 1H), 7.57-7.55 (m, 1H), 7.39 (t, J=7.7 Hz, 1H), 6.82-6.76 (m, 2H), 6.65-6.61 (m, 2H), 4.51 (hept, J=6.0 Hz, 1H), 3.90 (s, 3H), 3.88 (s, 2H), 3.27 (t, J=5.8 Hz, 2H), 2.91 (t, J=6.0 Hz, 2H), 1.34 (d, J=6.0 Hz, 6H). $^{13}$C NMR (100 MHz, CDCl$_3$): 167.1, 145.0, 140.7, 139.3, 132.661, 130.2, 129.4, 128.4, 128.3, 121.2, 116.4, 112.6, 110.3, 53.2, 52.0, 48.1, 43.4, 39.2, 23.3, 22.3.

B. N,N-Diethyl-3-{[2-(2-isopropoxy-phenylamino)-ethylamino]-methyl}-benzamide. To a solution of diethylamine (0.064 g, 0.88 mmol) in toluene (1 mL) was added trimethylaluminum (2.0 M in hexane, 0.044 mL, 0.88 mmol), and the resulting solution was stirred at 25° C. for 5 min. A solution of 3-{[2-(2-isopropoxy-phenylamino)-ethylamino]-methyl}-benzoic acid methyl ester (0.05 g, 0.146 mmol) in toluene (1 mL) was added, and the reaction mixture was stirred at 70° C. for 18 h. The mixture was partitioned with H$_2$O (10 mL) and EtOAc (20 mL). The organic layer was washed with 1 N NaOH (10 mL) then brine (10 mL), dried (MgSO$_4$), filtered, and concentrated under reduced pressure. The crude residue was purified by preparative TLC (10% CH$_3$OH/CH$_2$Cl$_2$) to provide a tan oil (0.083 g, 15%). MS (ESI): mass calculated for C$_{23}$H$_{33}$N$_3$O$_2$, 383.26; m/z found, 384.3 [M+H]$^+$, 406.3 [M+Na]$^+$. $^1$H NMR (400 MHz, CDCl$_3$): 7.39 (br d, J=7.5 Hz, 1H), 7.35-7.31 (m, 2H), 7.24 (br d, J=7.6 Hz, 1H), 6.83 (dt, J=7.6, 1.3 Hz, 1H), 6.78-6.76 (m, 1H), 6.65-6.61 (m, 2H), 4.52 (hept, J=6.1 Hz, 1H), 3.85 (s, 3H), 3.53 (br s, 2H), 3.28 (t, J=5.9 Hz, 2H), 3.23 (br s, 2H), 2.92 (t, J=6.0 Hz, 2H), 1.34 (d, J=6.1 Hz, 6H), 1.25-1.01 (br m, 6H). $^{13}$C NMR (100 MHz, CDCl$_3$): 171.2, 145.0, 140.0, 139.2, 137.4, 128.9, 128.5, 126.1, 124.9, 121.2, 116.5, 112.6, 110.3, 70.6, 53.2, 48.0, 43.1, 39.2, 22.3, 14.2, 12.9.

Example 38

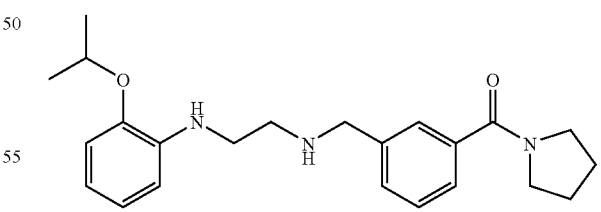

(3-{[2-(2-Isopropoxy-phenylamino)-ethylamino]-methyl}-phenyl)-pyrrolidin-1-yl-methanone The title compound was prepared as in Example 37, substituting pyrrolidine for diethylamine in step B. MS (ESI): mass calculated for C$_{23}$H$_{31}$N$_3$O$_2$, 381.2; m/z found, 382.3 [M+H]$^+$, 404.3 [M+Na]$^+$. $^1$H NMR (400 MHz, CDCl$_3$): 7.50 (br s, 1H), 7.43 (d, J=7.3 Hz, 1H), 7.39-7.31 (m, 2H), 6.83 (dt, J=7.6, 1.3 Hz, 2H), 6.78-6.76 (m, 2H), 6.65-6.61 (m, 2H), 4.52 (hept, J=6.0 Hz, 1H), 3.88 (s, 3H), 3.62 (t, J=6.9 Hz, 2H), 3.93 (t, J=6.7 Hz, 2H), 3.33 (t, J=6.0 Hz, 2H), 2.95 (t, J=6.0 Hz, 2H), 1.96-1.83 (br m, 4H), 3.45 (d, J=6.0 Hz, 6H). $^{13}$C NMR (100 MHz, CDCl$_3$): 169.5, 145.0, 139.0, 137.4, 129.9, 128.5, 127.1, 126.1, 121.2, 116.6, 112.6, 110.3, 70.6, 52.9, 49.6, 47.6, 46.2, 42.6, 26.3, 24.4, 22.3.

Example 39

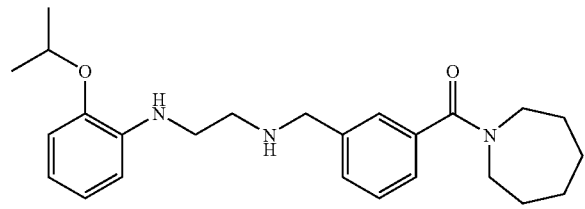

Azepan-1-yl-(3-{[2-(2-isopropoxy-phenylamino)-ethylamino]-methyl}-phenyl)methanone.

The title compound was prepared as in Example 37, substituting azepane for diethylamine in step B. MS (ESI): mass calculated for C$_{25}$H$_{35}$N$_3$O$_2$, 409.27; m/z found, 410.3 [M+H]$^+$, 432.3 [M+Na]$^+$. $^1$H NMR (400 MHz, CDCl$_3$): 7.40 (br d, J=7.6 Hz, 1H), 7.35-7.31 (m, 2H), 7.25 (br d, J=7.6 Hz, 1H), 6.83 (dt, J=7.7, 1.3 Hz, 1H), 6.78-6.76 (m, 1H), 6.65-6.61 (m, 2H), 4.52 (hept, J=6.1 Hz, 1H), 3.86 (s, 2H), 3.66 (t, J=5.9 Hz, 2H), 3.35-3.28 (m, 4H), 2.93 (t, J=6.0 Hz, 2H), 1.85-1.80 (m, 2H), 1.64-1.58 (m, 6H), 1.35 (d, J=6.0 Hz, 6H). $^{13}$C NMR (100 MHz, CDCl$_3$): 171.5, 145.0, 139.6, 137.4, 128.9, 128.5, 126.3, 125.2, 121.2, 116.5, 112.6, 110.3, 70.6, 53.1, 49.7, 47.9, 46.3, 43.0, 29.5, 27.3, 26.5, 22.3.

Example 40

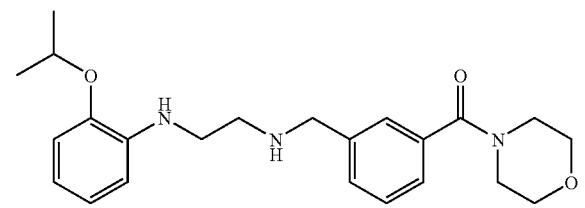

(3-{[2-(2-Isopropoxy-phenylamino)-ethylamino]-methyl}-phenyl)-morpholin-4-yl-methanone The title compound was prepared as in Example 37, substituting morpholine for diethylamine in step B. MS (ESI): mass calculated for C$_{23}$H$_{31}$N$_3$O$_3$, 397.24; m/z found, 398.3 [M+H]$^+$, 420.3 [M+Na]$^+$. $^1$H NMR (400 MHz, CDCl$_3$): 7.45-7.26 (m, 4), 6.83 (dt, J=7.7, 1.4 Hz, 1H), 6.77 (d, J=7.7 Hz, 1H), 6.66-6.62 (m, 2H), 4.52 (hept, J=6.0 Hz, 1H), 3.86 (s, 2H), 3.75-3.42 (br m, 8H), 3.29 (t, J=5.9 Hz, 2H), 2.93 (t, J=5.9 Hz, 2H), 1.35 (d, J=6.0 Hz, 6H). $^{13}$C NMR (100 MHz, CDCl$_3$): 170.3, 145.0, 140.2, 139.2, 135.4, 129.7, 128.6, 126.8, 125.8, 121.2, 116.6, 112.6, 110.3, 70.6, 66.9, 53.1, 48.0, 43.1, 22.3.

Example 41

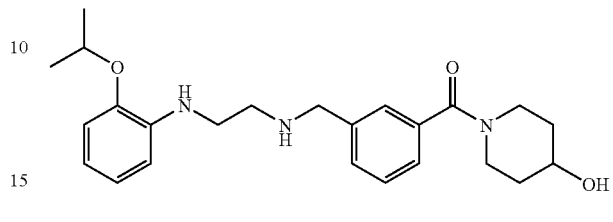

(4-Hydroxy-piperidin-1-yl)-(3-{[2-(2-isopropoxy-phenylamino)-ethylamino]-methyl}-phenyl)-methanone A. 3-(4-Hydroxy-piperidine-1-carbonyl)-benzaldehyde. The title intermediate was prepared as in Example 1, step D, substituting piperidin-4-ol for piperidine. MS (ESI): mass calculated for C$_{13}$H$_{15}$NO$_3$, 233.11; m/z found, 234.1 [M+H]$^+$. $^1$H NMR (400 MHz, CDCl$_3$): 8.02 (br s, 1H), 7.95-7.91 (m, 2H), 7.68 (d, J=7.5 Hz, 1H), 7.60 (t, J=7.5 Hz, 1H), 4.19 (br s, 1H), 4.04-4.10 (m, 1H), 3.65 (br s, 1H), 3.49 (br s, 1H), 3.47 (br s, 1H), 2.00-1.54 (m, 5H).

B. (4-Hydroxy-piperidin-1-yl)-(3-{[2-(2-isopropoxy-phenylamino)-ethylamino]-methyl}-phenyl)-methanone. The title compound was prepared as in Example 1, steps A-C and E, substituting 3-(4-hydroxy-piperidine-1-carbonyl)benzaldehyde for 3-(piperidine-1-carbonyl)-benzaldehyde in step E. MS (ESI): mass calculated for C$_{24}$H$_{33}$N$_3$O$_3$, 411.25; m/z found, 412.3 [M+H]$^+$. $^1$H NMR (400 MHz, CDCl$_3$): 7.36-7.24 (m, 3H), 7.18-7.16 (m, 1H), 6.79-6.75 (m, 1H), 6.72-6.70 (m, 1H), 6.59-6.55 (m, 2H), 4.45 (hept, J=6.1 Hz, 1H), 4.11 (br s, 1H), 3.90-3.84 (m, 1H), 3.80 (s, 2H), 3.50 (br s, 1H), 3.26-3.23 (m, 3H), 3.09 (br s, 1H), 2.89-2.86 (m, 2H), 1.89-1.72 (m, 2H), 1.53-1.40 (m, 2H), 1.28 (d, J=6.1 Hz, 6H).

Example 42

GlyT2 Inhibitory Activity

Assay Method

Cos-7 cells (African green monkey, kidney) from American Type Culture Collection were grown in DMEM supplemented with 10% fetal bovine serum. The entire coding region of the human GlyT2 cDNA was cloned into the mammalian expression vector pCINeo, and then stably transfected into Cos-7 cells. Transfection was performed essentially as described by T. W. Lovenberg et al. (Mol. Pharmacol. 1999, 55:1101-1107). Cells are grown to 70-80% confluence, removed from the plate with trypsin, and pelleted in a clinical centrifuge. The pellet is resuspended in 400 μL complete medium and transferred to an electroporation cuvette with a 0.4 cm gap between the electrodes (Bio-Rad, 165-2088). One microgram of supercoiled GlyT2 cDNA is added to the cells, and the suspension is mixed. The voltage for the electroporation is set at 0.25 kV, and the capacitance is set at 960 μF. After electroporation, the cuvette contents are diluted to 10 mL with complete medium, and 0.5 mL, 1.0 mL, 2.0 mL and remainder (~6.5 mL) portions are plated onto four 10-cm dishes. The cells are incubated 24 h before adding 600 μg/mL G418. Colonies that survive selection are isolated and tested for GlyT2 expression.

The day before the assay, the GlyT2 expressing cells were plated into 96-well scintillating microplates (Amersham, RPNQ 0160) at a density of approximately 20,000 cells per well. Cells were grown overnight at 37° C. in 5% $CO_2$ and then washed once with 37° C. HEPES buffered saline (HBS: 150 mM NaCl, 20 mM HEPES, 1 mM $CaCl_2$, 10 mM glucose, 5 mM KCl, 1 mM $MgCl_2$; pH 7.4). Eighty microliters of 37° C. HBS was subsequently added to each well. Test solutions of GlyT2 inhibitors were prepared in HBS from DMSO stock solutions, and 5 μL of test solution was added to each test well. Total transport and non-specific background were determined by adding 5 μL HBS or 5 μL 2 M glycine, respectively, to the appropriate control wells. Plates were then left at room temperature for 5 min before the addition of 20 μL of 100 μM $^{14}$C-glycine (NEN, NEC 048H) to each well for a final concentration of 20 μM. Plates were incubated for 2 h at 37° C. with 5% $CO_2$. After 2 h the reaction mixtures were removed by aspiration, and the plates were washed once with ice-cold HBS. Plates were sealed with TopSeal (Packard, 6005185) and counted on a Packard TopCount® scintillation counter.

TABLE 1

Compound Activity Summary

| EX | $IC_{50}$ (μM) |
|---|---|
| 1 | 0.4 |
| 2 | 4.0 |
| 3 | >10 |
| 4 | 20 |
| 5 | 2.5 |
| 6 | 3.0 |
| 7 | 1.2 |
| 8 | 3.0 |
| 9 | 0.8 |
| 10 | 1 |
| 11 | 5 |
| 12 | >10 |
| 13 | 0.55 |
| 14 | 3.1 |
| 15 | >10 |
| 16 | 3.1 |
| 17 | 1 |
| 18 | 3.1 |
| 19 | 1.2 |
| 20 | 3.1 |
| 21 | 2.5 |
| 22 | >10 |
| 23 | 0.955 |
| 24 | 0.4 |
| 25 | 0.4 |
| 26 | 7.5 |
| 27 | 11 |
| 28 | 3.5 |
| 29 | >10 |
| 30 | 1 |
| 31 | 1.6 |
| 32 | 10 |
| 33 | 4 |
| 34 | 3.1 |
| 35 | >10 |
| 36 | 3.1 |
| 37 | 10 |
| 38 | 3 |
| 39 | 1.8 |
| 40 | 10 |
| 41 | >10 |

What is claimed is:

1. A compound of the formula:

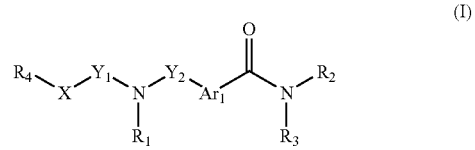

wherein $R_1$ is H or is a substituted or unsubstituted $C_{1-5}$ alkyl, $C_{1-5}$ alkenyl, or $C_{1-5}$ alkynyl;

$R_2$ and $R_3$ are taken together with the nitrogen of attachment to form piperidinyl, pyrrolidinyl, pyrrolinyl, tetrahydropyridinyl, dihydropyridinyl, azepanyl or morpholinyl, wherein each $R_2$ and $R_3$ substituent taken together, is optionally substituted with hydroxy or $C_{1-4}$alkoxy;

$R_4$ is phenyl optionally substituted at the 2 or 3 position with one or two $R^q$;

$Ar_1$ is thiophenediyl optionally substituted with $R^q$;

$Y_1$ and $Y_2$ are independently selected from a methylene or a ethylene;

X is S, O, or is $NR_1$, or alternatively, is a covalent bond; and $R^q$ is selected from the group consisting of —OH, —$C_{1-6}$ alkyl, —$OC_{1-6}$ alkyl, -Ph, -PhOH, -ureaPh, —OPh, benzyl, —Obenzyl, -ureabenzyl, thiophenyl, —$C_{3-6}$ cycloalkyl, —$OC_{3-6}$ cycloalkyl, —CN, —$NO_2$, —$N(R^y)R^z$ wherein $R^y$ and $R^z$ are independently selected from the group consisting of H, $C_{1-6}$alkyl and $C_{1-6}$ alkenyl, —(N—$R^t$)$COR^t$, —(N—$R^t$)$SO_2C_{1-6}$alkyl wherein $R^t$ is independently H or $C_{1-6}$alkyl —(C═O)$C_{1-6}$alkyl, —(S═(O)$_n$)—$C_{1-6}$alkyl wherein n is selected from 0, 1 or 2, —$SO_2N(R^y)R^z$, —$SCF_3$, halo, —$CF_3$, —$OCF_3$, —COOH and —$COOC_{1-6}$ alkyl;

and stereoisomers and pharmaceutically acceptable salts thereof.

2. A compound of claim 1, wherein:

$R_1$ is H; $R_2$ and $R_3$ together with the nitrogen of attachment form piperidinyl; $R_4$ is phenyl and is substituted at the 2 or 3 position with an —$OC_{1-6}$ alkyl or —$N(R^y)R^z$, wherein $R^y$ and $R^z$ are independently a $C_{1-6}$ alkyl; $Ar_1$ is thiophenediyl; $Y_1$ and $Y_2$ are the same or different and are methylene or ethylene; and X is NH or O.

3. A compound of claim 1, wherein:

$R_1$ is H; $R_2$ and $R_3$ together with the nitrogen of attachment form piperidinyl; $R_4$ is phenyl and is substituted at the 2 or 3 position with propoxy; $Ar_1$ is thiophenediyl; $Y_1$ is ethylene and $Y_2$ is methylene; and X is NH or O.

4. A compound of claim 1, wherein the compound is selected from the group consisting of:

(5-{[2-(2-Isopropoxy-phenylamino)-ethylamino]-methyl}-thiophen-3-yl)-piperidin-1-yl -methanone;

(5-{[2-(2-Amino-phenylamino)-ethylamino]-methyl}-thiophen-3-yl)-piperidin-1-yl -methanone; and (5-{[2-(2-Isopropylamino-phenylamino)-ethylamino]-methyl}-thiophen-3-yl)-piperidin -1-yl-methanone; and stereoisomers, pharmaceutically acceptable salts, thereof.

5. A pharmaceutical composition comprising a pharmaceutically acceptable carrier and an effective amount of a compound of the formula:

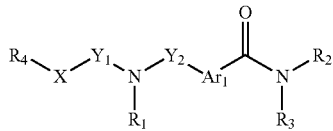

wherein
- $R_1$ is H or is a substituted or unsubstituted $C_{1-5}$ alkyl, $C_{1-5}$ alkenyl, or $C_{1-5}$ alkynyl;
- $R_2$ and $R_3$ are taken together with the nitrogen of attachment to form piperidinyl, pyrrolidinyl, pyrrolinyl, tetrahydropyridinyl, dihydropyridinyl, azepanyl or morpholinyl, wherein each $R_2$ and $R_3$ substituent taken together, is optionally substituted with hydroxy or $C_{1-4}$alkoxy;
- $R_4$ is phenyl optionally substituted at the 2 or 3 position with one or two $R^q$;
- $Ar_1$ is thiophenediyl, optionally substituted with $R^q$;
- $Y_1$ and $Y_2$ are independently selected from a methylene or a ethylene;
- X is S, O, or is $NR_1$, or alternatively, is a covalent bond; and
- $R^q$ is selected from the group consisting of —OH, —$C_{1-6}$ alkyl, —$OC_{1-6}$ alkyl, -Ph, -PhOH, -ureaPh, —OPh, benzyl, —Obenzyl, -ureabenzyl, thiophenyl, —$C_{3-6}$ cycloalkyl, —$OC_{3-6}$ cycloalkyl, —CN, —$NO_2$, —$N(R^y)R^z$ wherein $R^y$ and $R^z$ are independently selected from the group consisting of H, $C_{1-6}$alkyl and $C_{1-6}$alkenyl, $(C=O)N(R^y)R^z$, —(N—$R^t$)$COR^t$, —(N—$R^t$)$SO_2C_{1-6}$alkyl wherein $R^t$ is independently H or $C_{1-6}$alkyl —$(C=O)C_{1-6}$alkyl, —$(S=(O)_n)$—$C_{1-6}$alkyl wherein n is selected from 0, 1 or 2, —$SO_2N(R^y)R^z$, —$SCF_3$, halo, —$CF_3$, —$OCF_3$, —COOH and —$COOC_{1-6}$ alkyl;

and stereoisomers, and pharmaceutically acceptable salts, thereof.

6. The composition of claim 5 wherein said compound is selected from the group consisting of:
- (5-{[2-(2-Isopropoxy-phenylamino)-ethylamino]-methyl}-thiophen-3-yl)-piperidin-1-yl -methanone;
- (5-{[2-(2-Amino-phenylamino)-ethylamino]-methyl}-thiophen-3-yl)-piperidin-1-yl -methanone; and
- (5-{[2-(2-Isopropylamino-phenylamino)-ethylamino]-methyl}-thiophen-3-yl)-piperidin -1-yl-methanone; and stereoisomers, and pharmaceutically acceptable salts, thereof.

* * * * *